United States Patent
Tijssen et al.

(10) Patent No.: US 10,087,493 B2
(45) Date of Patent: Oct. 2, 2018

(54) METHOD FOR DETECTING INFECTIOUS PARVOVIRUS IN PHARMACEUTICAL PREPARATIONS

(75) Inventors: Peter Tijssen, Pointe-Claire (CA); Jozsef Szelei, Laval (CA); Zoltan Zadori, Montreal (CA)

(73) Assignee: APTALIS PHARMA CANADA ULC (CA)

(*) Notice: Subject to any disclaimer, the term of this patent is extended or adjusted under 35 U.S.C. 154(b) by 2 days.

(21) Appl. No.: 12/400,145

(22) Filed: Mar. 9, 2009

(65) Prior Publication Data
US 2009/0226414 A1 Sep. 10, 2009

Related U.S. Application Data

(60) Provisional application No. 61/034,847, filed on Mar. 7, 2008.

(51) Int. Cl.
| | | |
|---|---|---|
| *C12N 9/00* | (2006.01) | |
| *C12Q 1/70* | (2006.01) | |
| *C12N 15/10* | (2006.01) | |
| *C12Q 1/6806* | (2018.01) | |
| *G01N 33/569* | (2006.01) | |
| *A61K 38/46* | (2006.01) | |
| *A61K 38/47* | (2006.01) | |
| *A61K 38/48* | (2006.01) | |

(52) U.S. Cl.
CPC .............. *C12Q 1/70* (2013.01); *A61K 38/465* (2013.01); *A61K 38/47* (2013.01); *A61K 38/48* (2013.01); *C12N 15/1003* (2013.01); *C12Q 1/6806* (2013.01); *G01N 33/56983* (2013.01); *G01N 2333/015* (2013.01)

(58) Field of Classification Search
None
See application file for complete search history.

(56) References Cited

U.S. PATENT DOCUMENTS 3,844,891 A * 10/1974 Hess et al. .......... 435/186
4,079,125 A    3/1978 Sipos
(Continued)

FOREIGN PATENT DOCUMENTS

| CA | 2263703 A1 | 8/1999 |
|---|---|---|
| CA | 2419572 A1 | 8/2004 |

(Continued)

OTHER PUBLICATIONS

Mullendore et al., "Improved Method for the recovery of hepatitis A virus from oysters," Journal of Virological Methods 94, pp. 25-35 (2001).*

(Continued)

*Primary Examiner* — Janet L Andres
*Assistant Examiner* — M Franco G Salvoza
(74) *Attorney, Agent, or Firm* — Carter, DeLuca, Farrell & Schmidt, LLP

(57) ABSTRACT

The present invention provides methods for detecting viral infectivity and content in an enzyme preparation. In certain embodiments, the invention relates to methods for producing a pharmaceutical pancreatic enzyme composition. In additional embodiments, the invention relates to detecting infectious porcine parvovirus (PPV) and determining PPV content in pancreatic enzyme preparations (PEPs), including pancrelipase preparations.

3 Claims, 2 Drawing Sheets

Specification includes a Sequence Listing.

(56) References Cited

U.S. PATENT DOCUMENTS

| | | | |
|---|---|---|---|
| 4,237,229 A * | 12/1980 | Hartdegen et al. | 435/182 |
| 4,280,971 A | 7/1981 | Wischniewski et al. | |
| 4,447,412 A | 5/1984 | Bilton | |
| 4,704,295 A | 11/1987 | Porter et al. | |
| 4,786,505 A | 11/1988 | Lovgren et al. | |
| 4,849,227 A | 7/1989 | Cho | |
| 4,859,471 A | 8/1989 | Fulberth et al. | |
| 5,225,202 A | 7/1993 | Hodges et al. | |
| 5,260,074 A | 11/1993 | Sipos | |
| 5,306,506 A | 4/1994 | Zema et al. | |
| 5,324,514 A | 6/1994 | Sipos | |
| 5,378,462 A | 1/1995 | Boedecker et al. | |
| 5,460,812 A | 10/1995 | Sipos | |
| 5,570,104 A | 10/1996 | Hayashi | |
| 5,578,304 A | 11/1996 | Sipos | |
| 5,665,428 A | 9/1997 | Cha et al. | |
| 5,733,575 A | 3/1998 | Mehra et al. | |
| 5,733,763 A | 3/1998 | Markussen et al. | |
| 5,750,104 A | 5/1998 | Sipos | |
| 5,861,177 A | 1/1999 | Atzl et al. | |
| 5,861,291 A | 1/1999 | Abboudi et al. | |
| 6,051,220 A | 4/2000 | Scharpe | |
| 6,313,102 B1 | 11/2001 | Colaco et al. | |
| 6,318,650 B1 | 11/2001 | Breitenbach et al. | |
| 6,352,974 B1 | 3/2002 | Ghirri et al. | |
| 6,426,091 B1 | 7/2002 | Okumura et al. | |
| 6,607,747 B2 | 8/2003 | Ullah et al. | |
| 6,855,336 B2 | 2/2005 | Chen et al. | |
| 6,955,903 B2 | 10/2005 | Kulkarni et al. | |
| 7,201,923 B1 | 4/2007 | van Lengerich | |
| 7,658,918 B1 | 2/2010 | Ortenzi et al. | |
| 8,071,089 B2 | 12/2011 | Schuler et al. | |
| 8,221,747 B2 | 7/2012 | Ortenzi et al. | |
| 8,246,950 B2 | 8/2012 | Ortenzi et al. | |
| 8,293,229 B2 | 10/2012 | Ortenzi et al. | |
| 8,562,978 B2 | 10/2013 | Ortenzi et al. | |
| 8,562,979 B2 | 10/2013 | Ortenzi et al. | |
| 8,562,980 B2 | 10/2013 | Ortenzi et al. | |
| 8,562,981 B2 | 10/2013 | Ortenzi et al. | |
| 8,784,884 B2 | 7/2014 | Perrett et al. | |
| 2001/0024660 A1 | 9/2001 | Ullah et al. | |
| 2001/0046493 A1 | 11/2001 | Margolin et al. | |
| 2002/0044968 A1 | 4/2002 | van Lengerich | |
| 2002/0054907 A1 | 5/2002 | Devane et al. | |
| 2002/0187536 A1 | 12/2002 | Kulkarni et al. | |
| 2004/0057944 A1 | 3/2004 | Galle et al. | |
| 2004/0101562 A1 | 5/2004 | Maio | |
| 2004/0121010 A1 | 6/2004 | Hirsh et al. | |
| 2004/0197321 A1 | 10/2004 | Sipos et al. | |
| 2004/0213847 A1 | 10/2004 | Matharu et al. | |
| 2005/0019417 A1 | 1/2005 | Ko et al. | |
| 2005/0158299 A1 | 7/2005 | Margolin et al. | |
| 2005/0208133 A1 | 9/2005 | Tsutsumi et al. | |
| 2005/0281876 A1 | 12/2005 | Li et al. | |
| 2006/0121017 A1 | 6/2006 | Margolin et al. | |
| 2006/0198838 A1 | 9/2006 | Fallon | |
| 2007/0025977 A1 | 2/2007 | Mulberg | |
| 2007/0141151 A1 | 6/2007 | Silver et al. | |
| 2007/0148151 A1 * | 6/2007 | Frink et al. | 424/94.3 |
| 2007/0148152 A1 | 6/2007 | Shlieout et al. | |
| 2007/0190142 A1 | 8/2007 | Breitenbach et al. | |
| 2008/0199448 A1 | 8/2008 | Ross et al. | |
| 2008/0274174 A1 | 11/2008 | Ortenzi et al. | |
| 2008/0279839 A1 | 11/2008 | Schuler et al. | |
| 2008/0279953 A1 | 11/2008 | Ortenzi et al. | |
| 2008/0299185 A1 | 12/2008 | Ortenzi et al. | |
| 2009/0081184 A1 | 3/2009 | Margolin et al. | |
| 2009/0117180 A1 | 5/2009 | Ortenzi et al. | |
| 2009/0148545 A1 | 6/2009 | Falk et al. | |
| 2009/0226414 A1 | 9/2009 | Tijssen et al. | |
| 2009/0232789 A1 | 9/2009 | Fallon | |
| 2010/0021537 A1 | 1/2010 | Ortenzi et al. | |
| 2010/0239559 A1 | 9/2010 | Freedman et al. | |
| 2010/0270183 A1 | 10/2010 | Ortenzi et al. | |
| 2011/0064799 A1 | 3/2011 | Perrett et al. | |
| 2011/0123605 A1 | 5/2011 | Ortenzi et al. | |
| 2011/0123633 A1 | 5/2011 | Ortenzi et al. | |
| 2011/0123634 A1 | 5/2011 | Ortenzi et al. | |
| 2012/0177629 A1 | 7/2012 | Broussard et al. | |
| 2012/0201875 A1 | 8/2012 | Ortenzi et al. | |
| 2013/0251926 A1 | 9/2013 | Wood et al. | |
| 2014/0170212 A1 | 6/2014 | Ortenzi et al. | |
| 2014/0287035 A1 | 9/2014 | Perrett et al. | |
| 2014/0295474 A1 | 10/2014 | Latino et al. | |

FOREIGN PATENT DOCUMENTS

| | | |
|---|---|---|
| CN | 87103560 A | 5/1988 |
| CN | 1235824 A | 11/1999 |
| CN | 1376519 A | 10/2002 |
| CN | 1489476 A | 4/2004 |
| CN | 101430279 A | 5/2009 |
| DE | 2730481 A1 | 1/1978 |
| DE | 19907764 A1 | 11/1999 |
| EA | 201290985 A1 | 5/2013 |
| EP | 8780 A2 | 3/1980 |
| EP | 0035780 A1 | 9/1981 |
| EP | 0115023 A2 | 8/1984 |
| EP | 0256127 A1 | 2/1988 |
| EP | 0283442 A1 | 9/1988 |
| EP | 304332 A2 | 2/1989 |
| EP | 0576938 A1 | 1/1994 |
| EP | 0879772 A2 | 11/1998 |
| EP | 1010423 A2 | 6/2000 |
| EP | 1279402 A1 | 1/2003 |
| EP | 1335706 B1 | 4/2005 |
| EP | 1579771 A1 | 9/2005 |
| EP | 1931316 A2 | 6/2008 |
| EP | 1967211 A1 | 9/2008 |
| EP | 2079445 A2 | 7/2009 |
| EP | 2477645 A4 | 7/2012 |
| EP | 2621476 A1 | 8/2013 |
| EP | 2754437 A2 | 7/2014 |
| EP | 2818160 A1 | 12/2014 |
| ES | 489967 A1 | 10/1980 |
| FR | 2313916 A1 | 1/1977 |
| GB | 1509866 A | 5/1978 |
| JP | S52-3819 A | 1/1977 |
| JP | 58-085159 | 5/1983 |
| JP | H05-38731 A | 2/1993 |
| JP | 538731 | 10/1993 |
| JP | H05-76928 B2 | 10/1993 |
| JP | 10-295374 A | 11/1998 |
| JP | H11-514088 A | 11/1999 |
| JP | 2002506527 A | 2/2002 |
| JP | 2004-513645 A | 5/2004 |
| JP | 4187085 B2 | 11/2008 |
| JP | 2010519217 A | 6/2010 |
| KR | 100804096 B1 | 2/2008 |
| WO | 8705505 A1 | 9/1987 |
| WO | 90/09428 A1 | 8/1990 |
| WO | 9009440 A1 | 8/1990 |
| WO | 90/15856 A1 | 12/1990 |
| WO | 93/07859 A1 | 4/1993 |
| WO | 93/18753 A1 | 9/1993 |
| WO | 9325669 A1 | 12/1993 |
| WO | 9600773 A1 | 1/1996 |
| WO | 9746658 A1 | 12/1997 |
| WO | 98/01544 A1 | 1/1998 |
| WO | 97/46860 A3 | 2/1998 |
| WO | 98/58254 A1 | 12/1998 |
| WO | 01/25412 A1 | 4/2001 |
| WO | 01/70047 A1 | 9/2001 |
| WO | 0174980 A2 | 10/2001 |
| WO | 0240045 A2 | 5/2002 |
| WO | 02058735 A1 | 8/2002 |
| WO | 2004074470 A1 | 9/2004 |
| WO | 2005042012 A1 | 5/2005 |
| WO | 2005092370 A1 | 10/2005 |
| WO | 2006044529 A1 | 4/2006 |
| WO | 2007013752 A1 | 2/2007 |
| WO | 2007020259 A2 | 2/2007 |
| WO | 2007020260 A2 | 2/2007 |
| WO | 08/017659 A1 | 2/2008 |

(56) References Cited

FOREIGN PATENT DOCUMENTS

| WO | 2008102264 A2 | 8/2008 |
|---|---|---|
| WO | 2009109856 A2 | 9/2009 |
| WO | 2011035079 A1 | 3/2011 |
| WO | 2011072069 A2 | 6/2011 |
| WO | 2011114224 A1 | 9/2011 |
| WO | 2012019186 A1 | 2/2012 |
| WO | 2012042372 A1 | 4/2012 |
| WO | 2012052853 A1 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |

OTHER PUBLICATIONS

Sair et al., "Improved detection of human enteric viruses in foods by RT-PCR," Journal of Virological Methods 100, pp. 57-69 (2002).*
Guevremont et al., "Development of an extraction and concentration procedure and comparison of RT-PCR primer systems for the detection of hepatitis A virus and norovirus GII in green onions," Journal of Virological Methods 134: pp. 130-135 (2006).*
Casas et al. "Detection of enterovirus and hepatitis A virus RNA in mussels (*Mytilus* spp.) by reverse transcriptase-polymerase chain reaction," Journal of Applied Microbiology 90: 89-95 (2001).*
Schwab et al., "Concentration and Purification of Beef Extract Mock Eluates from Water Samples for the Detection of Enteroviruses, Hepatitis A Virus, and Norwalk Virus by Reverse Transcription-PCR," Applied and Environmental Microbiology, vol. 61, No. 2: 531-547 (1995).*
Tolin et al., "Purification and Serology of Peanut Mottle Virus," Phytopathology 73: 899-903 (1983).*
Lewis et al., "Polyethylene Glycol Precipitation for Recovery of Pathogenic Viruses, Including Hepatitis A Virus and Human Rotavirus, from Oyster, Water, and Sediment Samples," Applied and Environmental Microbiology, vol. 54, No. 8: 1983-1988 (1988).*
Takanami et al., "Enzyme-assisted Purification of two Phloem-limited Plant Viruses: Tobacco Necrotic Dwarf and Potato Leafroll," J. Gen. Virol., 44: 153-159 (1979).*
Bergeron et al., "Genomic organization and mapping of transcription and translation products the NADL-2 strain of porcine parvovirus", Virology, 1993, 197(1):86-98.
Bergeron, J., Hebert, B. & Tijssen, P. (1996). Genome organization of the Kresse strain of porcine parvovirus: identification of the allotropic determinant and comparison with those of NADL-2 and field isolates. Journal of Virology 70, 2508-2515.
Simpson et al., "The structure of porcine parvovirus: comparison with related viruses.", J. Mol. Biol., 2002 315(5):1189-98.
Szelei et al., "Porcine parvovirus". In: Kerr, et al., eds, Parvoviruses, London: Hodder Arnold; 2006. pp. 434-445.
Canaan, et al, 2004. "Interfacial Enzymology of Parvovirus Phospholipases $A_2$". Journal of Biological Chemistry 279(15): 14502-14508.
Zadori, et al, 2001. "A Viral Phospholipase $A_2$ Is Required for Parvovirus Infectivity". Developmental Cell 1: 291-302.
Zadori, et al, 2005. "SAT: a Late NS Protein of Porcine Parvovirus". Journal of Virology 79(20): 13129-13138.
Sincero, et al. "Detection of hepatitis A virus (HAV) in oysters (*Crassostrea gigas*)" Water Research , Elsevier, Amsterdam, NL, vol. 40, No. 5, Mar. 1, 2006, pp. 895-902.
Langeveld, et al: "Inactivated recombinant plant virus protects dogs from a lethal challenge with canine parvovirus" Vaccine, Butterworth Scientific Guildford, GB, vol. 19, No. 27, Jun. 14, 2001, pp. 3661-3670.
Singh, et al: "Canine parvovirus-like particles, novel nanomaterial for tumor targeting" Journal of Nanobiotechnology 2006, vol. 4, No. 2. Published Feb. 13, 2006. doi:10.1186/1477-3155-4-2.

Shieh, et al.: "A method to detect low levels of enteric virus in contaminated oysters" Applied and environmental Microbiology, vol 65, No. 11, Nov. 1999, pp. 4709-4714.
A. C. Mehta, "Review of analytical methods used in the dissolution testing of pharmaceuticals", Analytical Proceedings Including Analytical Communications, vol. 31, No. 8, Jan. 1, 1994; pp. 245-248.
Alexey Khrenov: "USP Pancrelipase Update," dated Jul. 1, 2009, and Alexey Khrenov: "USP Enzyme Workshop: Pancrelipase Update," dated Jul. 1, 2009; 12 total pages.
"Dissolution Toolkit—Procedures for Mechanical Calibration and Performance Verification Test," USP (U.S, Pharmacopeia), dated Mar. 22, 2010; 16 pages.
New Zealand First Examination Report, dated Oct. 16, 2014, corresponding to New Zealand Application No. 620329; 2 pages.
Colombian Office Action (with English Translation), dated Oct. 29, 2014, corresponding to Colombian Application No. 14-33910; 20 total pages.
Coutlee, et al., "Comparison of Colorimetric, Fluorescent, and Enzymatic Amplification Substrate Systems in an Enzyme Immunoassay for Detection of DNA-RNA Hybrids," Journal of Clinical Microbiology, vol. 27, No. 5, May 1989; pp. 1002-1007.
Fuhrmann, et al., "In Vivo Fluorescence Imaging of Exogenous Enzyme Activity in the Gastrointestinal Tract," Proceedings of the National Academy of Sciences of the USA, vol. 108, No. 22, May 2011; pp. 9032-9037.
Zhang, et al., "Quantitative Fluorescence Correlation Spectroscopy Reveals a 1000-Fold Increase in Lifetime of Protein Functionality," Biophysical Journal, vol. 95, Oct. 2008; pp. 3439-3446.
(Guidance for Industry) "SUPAC-MR: Modified Release Solid Oral Dosage Forms—Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997; 52 pages.
Australian Patent Examination Report No. 1, dated May 20, 2014, corresponding to Australian Application No. 2012293325; 3 pages.
Chinese Office Action (with No English translation), dated Dec. 2, 2014, corresponding to Chinese Application No. 201280040203.2; 6 pages.
Colombian Office Action (English Summary), corresponding to Colombian Application No. 13-66300; 2 pages.
Eurasian Office Action (with English Translation), dated Jun. 30, 2014, corresponding to Eurasian Application No. 201390409; 5 total pages.
Handbook of Pharmaceutical Excipients, Fifth Edition, Edited by Raymond C. Rowe, et al. 4 pages.
Australian Patent Examination Report No. 1, dated Oct. 14, 2014, corresponding to Australian Application No. 2011309763; 3 pages.
European Search Report, dated Nov. 28, 2014, corresponding to European Application No. 14176579.2; 4 pages.
English translation of Colombian Office Action, corresponding to Colombian Application No. 13-066300; 7 pages.
Chinese Office Action (With No English translation), dated Jan. 6, 2015, corresponding to Chinese Application No. 201180055719.X; 18 pages.
Masaki Hasegawa, Direct Compression "Microcrystalline Cellulose Grade 12 versus Classic Grade 102," Pharmaceutical Technology, May 2002; pp. 50-60.
Australian Patent Examination Report No. 1, dated Apr. 28, 2014, corresponding to Australian Application No. 2010295494; 3 pages.
Extended European Search Report, dated May 26, 2014, corresponding to European Application No. 10817867.4; 6 pages.
Symersky T., et al. "An Explorative Study on the Effect of Enzyme Supplementation in Patients Recovered From Acute Pancreatitis," Gastroenterology 2004; 126 (4 suppl 2): A85, Abstract 653.
Taiwanese Office Action (with No English translation), dated Jul. 21, 2014, corresponding to Taiwanese Application No. 099131496; 6 pages.
Taiwanese Search Report (with No English translation, dated Jul. 16, 2014, corresponding to Taiwanese Application No. 099131496; 1 page.
Russian Office Action (with English Translation), dated Jul. 7, 2014, corresponding to Russian Application No. 2012113253; 8 total pages.

(56) References Cited

OTHER PUBLICATIONS

Colombian Office Action (with No English Translation), dated Aug. 22, 2014, corresponding to Colombian Application No. 12-50658; 9 pages.
Chilean Office Action (with No English Translation), dated Oct. 8, 2014, corresponding to Chilean Patent Application No. 00658-2012; 8 pages.
Japanese Notice of Rejection (with English Summary Translation), dated Sep. 24, 2014, corresponding to Japanese Application No. 2012-529909; 6 pages.
Chinese Office Action (with No English translation), dated Nov. 24, 2014, corresponding to Chinese Application No. 201080041366.3; 3 pages.
Russian Office Action (with English translation), dated Nov. 25, 2014, corresponding to Russian Application No. 2012113253; 11 total pages.
Taiwanese Office Action (with English translation), dated Nov. 26, 2014, corresponding to Taiwanese Application No. 099131496; 10 total pages.
Pakistan Examination Report, corresponding to Pakistan Application No. 804/2010; 1 page.
English translation of Israeli Office Action, dated Nov. 23, 2014, corresponding to Israeli Application No. 218656; 2 pages.
Eurasian Office Action (with English Translation), dated Jan. 30, 2015, corresponding to Eurasian Application No. 201390409/28; 4 total pages.
Avicel-FMC, Avicel product sheet, Apr. 22, 2010.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-2009-7019590; 6 total pages.
Non-patent literature cited during the Appeal Procedure (universitatbonn) (D22), dated Jun. 17, 2010; 6 pages.
Non-patent literature relating to the Appeal Procedure, dated Aug. 5, 2010, (Eisenfuhr Speiser); 10 pages.
Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Kahn, et al., Bovine Pancreatic Lipase1. II. Stability and Effect of Activators and Inhibitors, Journal of Dairy Science, vol. 59, No. 5, pp. 840-846.
Worthington Biochemical Corporation, Lipase—Worthington Enzyme Manual, Triacylglycerol acylhydrolase, (D14); www.worthington-biochem.com; 2 pages.
Caelo, Macrogol 4000 Pulver, Sicherheitsdatenblatt, Seite1, von 3, (D15), dated Aug. 4, 2008; 3 pages.
Answers.com, Stir: Definition, Synonyms of the word "Stir" from Answers.com, (D16), 9 pages.
Office Action issued by the U.S. Patent and Trademark Office dated Apr. 1, 2009, corresponding to U.S. Appl. No. 10/416,702, 24 pages.
US Pharmacopeia, Chapter 786, Particle Size Distribution Estimation by Analytical Sieving, Web download, Jun. 26, 2009; 5 pages.
Gohel, "A Review of Co-Processed Directly Compressible Excipients," J. Pharm. Pharmaceutical Sciences, 8(1); pp. 76-93; (2005).
Priority Document, Italian Patent No. MI2000 A 002456, 25 pages.
Non-patent literature cited during the Appeal Procedure, Eisenfuhr Speiser, Feature Analysis, dated Aug. 5, 2010; 1 page.
Final Office Action issued by the U.S. Patent and Trademark Office dated Jul. 14, 2008, corresponding to U.S. Appl. No. 10/416,702, 12 pages.
Fuhrmann, Vorlesungen uber, Technische Mykologie, Verlag Gustav Fisher 1913, 80; (D19); 4 pages.
Mesh to Micron Conversion Chart—Fluideng.com, Copyright 2002—Property of TM Industrial Supply, Inc.; (D20); http://www.fluideng.com/Fe/meshmicron.html; 1 page.
English Translation of Example 3 of Priority Document IT M12000A002455, Preparation of Pancreatin Pellets Through Direct Spheronisation in Fluid Bed (D21); 1 page.
Summary of facts and submissions, Grounds for the Decision (Annex)—opposition, corresponding to Application No. 01 994 654.0, dated Feb. 23, 2009; 9 pages.
Interlocutory Decision in Opposition proceedings, corresponding to Application No. 01 994 654.0-2107, dated Feb. 23, 2009; 2 pages.
Non-patent literature cited during the Appeal Procedure, related to EP 1 335 706 B1 (Druckexemplar); 8 pages.
Provision of the minutes in accordance with Rule 124(4) EPC, dated Feb. 23, 2009, corresponding to Application No. 01 994 654.0-2107; 12 pages.
Non-patent literature, dated Jul. 30, 2012, relating to the Appeal Procedure, (Eisenfuhr Speiser); 7 pages.
Letter from Botti & Ferrari, dated Jun. 27, 2012, relating to the Appeal Procedure, 10 pages.
Non-patent literature cited during the Appeal Procedure, (Eisenfuhr Speiser), Grounds of Appeal, dated Jun. 30, 2009; 24 pages.
Letter from Botti & Ferrari, dated Sep. 18, 2009, relating to the Appeal Procedure, 15 pages.
Main Request, Claims with revisions, relating to Appeal Procedure; 1 page.
Description, relating to EP 1 335 706, relating to the Appeal Procedure; 1 page.
Main Request, Claims 1-7, relating to Appeal Procedure; 2 pages.
Royce, et al., Alternative Granulation Technique: Melt Granulation, Drug Development and Industrial Pharmacy, (D4) 22(9&10), 917-924; Copyright 1996 by Marcel Dakker, Inc.
Lombroso, "About the Destruction of the Pancreatic Enzymes by Means of Heat and the Substances that Hamper Such Action", Archivio di Farmacologia Sperimentale e Scienze Affini, Laboratory of Physiology of the R. University of Rome; 14 pages.
Novozymes—Savinase, novozymes, Rethink Tomorrow, Annex 1, A Hard-working, robust protease used to remove protein-based stains; 1 page.
Notice of Opposition to a European Patent and opposition documents related to Patent No. EP 1 335 706 B1, (Opposition file history as of Jan. 14, 2009, excluding non-duplicative, non-administrative documents; (92 total pages).
Non-patent literature dated Sep. 30, 2011, relating to the Appeal Procedure, (Eisenfuhr Speiser); 2 pages.
Non-patent literature cited during the Appeal Procedure, (universitatbonn) (D23), dated Sep. 20, 2011; 15 pages.
Non-patent literature cited during the Appeal Procedure, (One Step Ahead, Granulation and drying for all types of products), Rotolab, (D24); 8 pages.
Sincero, et al., "Detection of hepatitis A virus (HAV) in oysters (*Crassostrea gigas*)," Water Research, Elsevier, Amsterdam, NL, vol. 40, No. 5, Mar. 1, 2006; pp. 895-902.
Langeveld, et al, "Inactivated recombinant plant virus protects dogs from a lethal challenge with canine parvovirus," Vaccine, Elsevier, vol. 19, No. 27, Jun. 14, 2001, pp. 3661-3670.
Singh, et al., "Canine parvovirus-like particles, a novel nanomaterial for tumor targeting," Journal of Nanobiotechnology 2006, vol. 4, No. 2, dated Feb. 13, 2006; 11 pages.
Shieh, et al., "A method to detect low levels of enteric virus in contaminated oysters", Applied and environmental Microbiology, vol. 65, No. 11, Nov. 1999; pp. 4709-4714.
Bergeron, et al., Genomic Organization and Mapping of Transcription and Translation Products of the NADL-2 Strain of Porcine Parvovirus, Virology, 1993, 197(1): pp. 86-98.
Bergeron, J., Hebert, B. and Tijssen, P., Genomic Organization of the Kresse Strain of Porcine Parvovirus: Identification of the Allotropic Determinant and Comprison with Those of NADL-2 and Field Isolates, Journal of Virology vol. 70, No. 4, Apr. 1996; pp. 2508-2515.
Simpson, et al., "The Structure of Porcine Parvovirus: Comparison With Related Viruses," J. Mol. Biol., 2002, 315(5); pp. 1189-1198.

(56) References Cited

OTHER PUBLICATIONS

Szelei, et al., "Porcine Parvovirus". In: Kerr, et al., eds, Parvoviruses, London: Hodder Arnold; 2006; pp. 434-445.
Canaan, et al., "Interfacial Enzymology of Parvovirus Phospholipases A2," Journal of Biologizal Chemistry vol. 279, No. 15, Apr. 9, 2004; pp. 14502-14508.
Zadori, et al., 2001, "A Viral Phospholipase A2 is Required for Parvovirus Infectivity," Developmental Cell, vol. 1, Aug. 2001; pp. 291-302.
Zadori, et al., "SAT: a Late NS Protein of Porcine Parvovirus," Journal of Virology, vol. 79, No. 20; Oct. 2005; pp. 13129-13138.
Mullendore, et al., Improved Method for the Recovery of Hepatitis A virus from oysters, Journal of Virological Methods 94, pp. 25-35 (2001).
Sair, et al., "Improved Detection of Human Enteric Viruses in Foods by RT-PCR", Journal of Virological Methods 100, pp. 57-69 (2002).
Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).
Termination of Opposition Proceedings of Patent No. 01994654.0-1456/ 1335706 with Revocation of the Patent, dated May 14, 2014; 2 pages.
International Search Report, dated Jun. 23, 2014, corresponding to International Application No. PCT/IB2014/059722; 4 pages.
Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.
Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.
International Search Report and Written Opinion of the International Searching Authority, dated Mar. 2, 2015, corresponding to International Application No. PCT/IB2014/002583; 13 total pages.
Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.
International Search Report, and Written Opinion of the International Searching Authority, corresponding to International Application No. PCT/US14/49569, dated Nov. 14, 2014; 8 total pages.
Queensland Government, "Tube Feeding at Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009, 15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
International Search Report and Written Opinion of the International Searching Authority, corresponding to International Application No. PCT/US14/63984, dated Mar. 13, 2015; 10 total pages.
Chinese First Office Action and Search Report (English translations), dated Apr. 3, 2015, corresponding to Chinese Patent Application No. 201410059861.7; 23 total pages.
Israeli Office Action dated May 10, 2015 (No English translation), corresponding to Israeli Patent Application No. 200407; 2 pages.
European extended Search Report, dated Jun. 2, 2015, corresponding to European Patent Application No. 14150794.7; 10 pages.
Japanese Office Action (No English translation), dated May 12, 2015, corresponding to Japanese Patent Application No. 2013-530811; 3 pages.

U.S. Appl. No. 14/209,365, filed Mar. 13, 2014, cited herewith as U.S. Patent Publication No. 2014/0276632.
International Search Report, Written Opinion and International Preliminary Report on Patentability based on International Application No. PCT/IB2008/000770, dated Jun. 3, 2009; 13 Pages.
Krishnamurty et al., "Delayed release pancrelipase for treatment of pancreatic exocrine insufficiency associated with chronic pancreatitis," Therapeutics and Clinical Risk Management, (May 2009) pp. 507-520.
Drugs@FDA Glossary of Terms, printed Nov. 20, 2009; http://www.fda.gov/Drugs/InformationonDrugs/ucm079436.htm; 7 pages.
Guidance for Industry #191, Changes to Approved NADAs—New NADAs vs. Category II Supplemental NADAs, Final Guidance, U.S. Department of Health and Human Services, Food and Drug Administration, Center for Veterinary Medicine, Released Nov. 19, 2009: 25 pages.
Singapore Written Opinion, corresponding to Singapore Patent Application No. 200905385-1, issued by the Austrian Patent Office dated Dec. 16, 2010; 6 pages.
Hageman, "The Role of Moisture in Protein Stability," Drug Development and Industrial Pharmacy, vol. 14, No. 14, (1988); pp. 2047-2070.
Maul and Schmidt, "Influence of different-shaped pigments on bisacodyl release from Eudragit L 30 D," International Journal of Pharmacetuics, vol. 118, No. 1, May 1, 1995; pp. 103-112.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, pp. 498-506.
Felton and McGinity, "Influence of Insoluble Excipients on Film Coating Systems," Drug Development and Industrial Pharmacy, vol. 28, No. 3; pp. 225-243.
Parker et al., "Effects of Solids-Loading on Moisture Permeability Coefficients of Free Films," Journal of Pharmaceutical Sciences, vol. 63, No. 1 (Jan. 1974); pp. 119-125.
Thoma and Bechtold, "Influence of aqueous coatings on the stability of enteric coated pellets and tablets," European Journal of Pharmaceutics and Biopharmaceutics, vol. 47, (1999), pp. 39-50.
Nordmark pancreatin brochure, Products all over the World, (publication year unknown); 7 pages.
Australian First Examination Report, dated Mar. 23, 2012, corresponding to Australian Patent Application No. 2008218595; 2 pages.
English Translation of Second Chinese Office Action, dated Apr. 12, 2012, corresponding to Chinese Patent Application No. 200880012762.6; 5 pages.
European Communication, dated Jan. 3, 2012, corresponding to European Patent Application No. 08719392.6; 7 pages.
European Communication, dated Aug. 1, 2012, corresponding to European Patent Application No. 08719392.6; 7 pages.
New Zealand First Examination Report, dated Aug. 26, 2010, corresponding to New Zealand Patent Application No. 579047; 3 pages.
New Zealand Second Examination Report, dated Dec. 15, 2011, corresponding to New Zealand Patent Application No. 579047; 2 pages.
New Zealand First Examination Report, dated Feb. 29, 2012, corresponding to New Zealand Patent Application No. 598477; 1 page.
Singapore Second Written Opinion, dated Nov. 22, 2011, corresponding to Singapore Patent Application No. 200905385-1; 6 pages.
U.S. Office Action, dated Mar. 20, 2012, corresponding to U.S. Appl. No. 12/034,480; 7 pages.
U.S. Office Action, dated Oct. 14, 2011, corresponding to U.S. Appl. No. 12/034,480; 15 pages.
U.S. Office Action, dated Mar. 19, 2012, corresponding to U.S. Appl. No. 12/034,488; 8 pages.
U.S. Office Action, dated Oct. 25, 2011, corresponding to U.S. Appl. No. 12/034,488; 14 pages.
U.S. Office Action, dated Jan. 4, 2012, corresponding to U.S. Appl. No. 12/034,491; 7 pages.

(56) References Cited

OTHER PUBLICATIONS

U.S. Office Action, dated Jun. 23, 2011, corresponding to U.S. Appl. No. 12/034,491; 7 pages.
U.S. Office Action, dated Jun. 26, 2012, corresponding to U.S. Appl. No. 13/019,844; 15 pages.
U.S. Office Action, dated May 24, 2012, corresponding to U.S. Appl. No. 13/019,856; 9 pages.
U.S. Office Action, dated May 23 2012, corresponding to U.S. Appl. No. 13/019,860; 5 pages.
U.S. Office Action, dated Jul. 2, 2012, corresponding to U.S. Appl. No. 12/832,596; 11 pages.
International Search Report and Written Opinion, dated Oct. 22, 2012, corresponding to International Application No. PCT/US2010/049203; 6 pages.
Canadian Office Action, dated May 6, 2014, corresponding to Canadian Application No. 2,677,989, 2 pages.
Colombian Office Action (with No English translation), dated May 26, 2014, corresponding to Colombian Application No. 09.101.677; 4 pages.
Costa Rica Preliminary Technical Report—1st Phase (with English Translation), dated Jun. 12, 2014, corresponding to Costa Rican Application No. 11031; 11 total pages.
European Communication, dated Apr. 8, 2014, corresponding to European Patent Application No. 08719392.6; 6 pages.
English Translation of Indian First Examination Report, dated Oct. 17, 2014, corresponding to Indian Application No. 5854/DELNP/2009; 4 pages.
Singapore Search Report, dated Apr. 7, 2014 and Singapore Written Opinion, dated Apr. 28, 2014, corresponding to Singapore Application No. 2012091583; 11 total pages.
Japanese Decision of Rejection and Decision of Dismissal of Amendment (with English Translations), dated Aug. 25, 2014, corresponding to Japanese Application No. 2009-549868; 9 total pages.
Japanese Notice of Reasons for Rejection (with English translation), dated Jan. 19, 2015, corresponding to Japanese Application No. 2013-265143, 7 total pages.
Taiwanese Search Report (with English translation) and Taiwanese Office Action (with No English translation), dated Oct. 3, 2014, corresponding to Taiwanese Application No. 102138934; 10 total pages.
Colombian Office Action (with No English translation), dated Sep. 23, 2014, corresponding to Colombian Application No. 14.026.502, 4 pages.
The Decision of the Enlarged Board of Appeal, dated Nov. 22, 2013, 18 pages.
The Minutes of the Oral Proceedings of Nov. 22, 2013, 6 pages.
Communication from the Enlarged Board of Appeal pursuant to Articles 13 and 14(2) RPEBA, corresponding to Case No. R 06/13, dated Sep. 17, 2013; 6 pages.
Letter from Botti & Ferrari regarding a Petition for Review of Decision T0977/09-3.3.02, European Patent No. 1 335 706 in the name of Aptalis Pharma S.r.I., dated May 15, 2013; 12 pages.
Termination of Opposition Proceedings of Patent No. 01994654.0-1456 / 1335706 with Revocation of the Patent, dated Mar. 14, 2013; 2 pages.
Decision, dated Nov. 30, 2012, corresponding to Appeal No. T0977/09-3.3.02; 28 pages.
The Minutes of the Oral Proceedings of Nov. 30, 2012, corresponding to Appeal No. T0977/09-3.3.02; 18 pages.
International Search Report, International Preliminary Report on Patentability and Written Opinion of the International Searching Authority, corresponding to International Application No. PCT/IB2012/054050, dated Nov. 14, 2012; 11 total pages.
A. Aloulou, et al., "In Vitro Comparative Study of Three Pancreatic Enzyme Preparations: Dissolution Profiles, Active Enzyme Release and Acid Stability," Alimentary Pharmacology & Therapeutics, vol. 27, No. 3; Oct. 29, 2007; pp. 283-292.

International Preliminary Report on Patentability and Written Opinion of the International Searching Authority, dated Jan. 26, 2016, corresponding to International Application No. PCT/IB2014/002583; 10 total pages.
European Search Report dated Jan. 22, 2016, corresponding to European Application No. 15178147.3; 9 pages.
Communication of the Board of Appeal, corresponding to Appeal No. T2255/12-33.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Botti & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patent No. 1 931 316, dated May 2, 2012; 1 page.
Non-Patent Literature document—"Submission in opposition proceedings," issued by the European Patent Office, corresponding to European Patent No. 1 931 316, dated May 2, 2012; 1 page.
Non-Patent Literature document—"Reply to summons to attend oral proceedings; filing of new main claim request," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1(2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Non-Patent Literature document—"Notice of Opposition against the European Patent EP-B-1 931 316", (letter from Botti & Ferrari to the European Patent Office), dated Nov. 15, 2010, 12 pages.
Colombian Office Action (No English translation available), dated Feb. 19, 2016, corresponding to Colombian Application No. 14-026502; 8 pages.
Non-Patent Literature Document—"Aqueous Coating—Aquacoat ECD," FMC Biopolymer; 12 pages.
Non-Patent Literature document—"Brief Communication," dated Feb. 10, 2011, issued by the European Patent Office, corresponding to European Application No. 06778240.9 (European Patent No. 1 931 316); 1 page.

(56) References Cited

OTHER PUBLICATIONS

Non-Patent Literature document—"Claims—First Auxiliary Request" and "Claims—Second Auxiliary Request," dated Sep. 2011, corresponding to Opposition Proceedings of European Patent No. 1 931 316; 12 total pages.
Non-Patent Literature document—"Brief Communication—Main Request,", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to European Patent No. 1 931 316, dated Jan. 21, 2010; 2 pages.
Non-Patent Literature document—"A2PAMPHLET," related to WO 2007/020259 (PCT/EP2006/065311), printed on May 19, 2008; 29 total pages.
Non-Patent Literature document—"Claims (EP 06 778 240)," printed Sep. 25, 2008; 12 total pages.
Naftifine HCI—MSDS—Material Safety Data Sheet, created Jun. 23, 2004; http://pharmacycode.com/msds/Naftifine_HCI; 4 pages.
Australian Patent Examination Report No. 2, dated Feb. 25, 2016, corresponding to Australian Application No. 2014203364; 5 pages.
Japanese Office Action (with English translation), dated Mar. 1, 2016, corresponding to Japanese Application No. 2014-524476; 5 total pages.
Chinese Office Action (No English translation available), dated Feb. 15, 2016, corresponding to Chinese Application No. 201180055719.X; 14 pages.
"Polymer Science in Pharmaceutics", Junmin Zheng, China Medical Science Press, pp. 113-114, Jan. 31, 2009)—Article Unavailable.
International Preliminary Report on Patentability and Written Opinion of the International Searching Authority, dated Feb. 9, 2016, corresponding to International Application No. PCT/US2014/049569; 7 total pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Malaysian Office Action dated Mar. 31, 2016, corresponding to Malaysian Application No. PI 2012001215; 3 pages.
Israeli Office Action (No English translation available), dated Apr. 3, 2016, corresponding to Israeli Application No. 218656; 2 pages.
Sankalia M.G. et al., "Papain Entrapment in Alginate Beads for Stability Improvement and Site-Specific Delivery: Physicochemical Characterization and Factorial Optimization Using Neural Network Modeling," AAPS PharmSciTech., 2005; vol. 6, No. 2, Article 31; pp. E209-E222.
Scheich C. et al., "An Automated In Vitro Protein Folding Screen Applied to a Human Dynactin Subunit," Protein Science, 2004, vol. 13; pp. 370-380.
Miller D.A. et al., "Evaluation of the USP Dissolution Test Method A for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; pp. 12488-12496.
Canadian Office Action dated Jul. 3, 2015, corresponding to Canadian Patent Application No. 2,774,269; 4 pages.
Japanese Final Office Action (No English translation), dated Jul. 7, 2015, corresponding to Japanese Patent Application No. 2012-529909; 3 pages.
International Written Opinion of the International Searching Authority and International Search Report dated Jan. 19, 2010, corresponding to International Application No. PCT/IB2009/000472; 7 total pages.

Communication of a Notice of Oppoistion to a European Patent Application and opposition documents related to Patent Application No. EP 117885223.3, dated Aug. 5, 2015 (678 total pages).
Arbocel Product Sheet.
Russian Office Action (with English translation), dated Oct. 29, 2015, corresponding to Russian Application No. 2014104591; 7 total pages.
English translation of Israeli Office Action dated Jan. 11, 2016, corresponding to Israeli Patent Application No. 225504; 3 pages.
Eurasian Office Action (With English Translation) dated Oct. 30, 2015, correpsonding to Eurasian Application No. 201390409/28; 4 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
International Search Report and Written Opinion of the International Searching Authority dated Nov. 20, 2015, corresponding to International Application No. PCT/IB2015/001237; 17 total pages.
Japanese Office Action (with English translation), dated May 12, 2015, corresponding to Japanese Patent Application No. 2013-530811; 8 total pages.
U.S. Appl. No. 61/389,037, filed Oct. 1, 2010 (prosecution history).
Russian Office Action (with English translation), dated Jun. 15, 2015, corresponding to Russian Patent Appplication No. 2014104591/15; 10 total pages.
European Communication dated Jul. 6, 2015, corresponding to European patent application No. 14150794.7; 2 pages.
Korean Notice of Preliminary Rejection (with English translation), dated Jun. 12, 2015, corresponding to Korean patenl application No. 10-2015-7004820; 16 total pages.
Australian Patent Examination Report No. 1, dated Jul. 6, 2015, corresponding to Australian Patent Application No. 2014203364; 4 pages.
Canadian Office Action and Examination Search Report dated Sep. 3, 2015, corresponding to Canadian Patent Application No. 2,677,989; 4 total apges.
Japanese Decision of Rejection (with English translation) dated Sep. 25, 2015, corresponding to Japanese Applcation No. 2013-265143; 9 total pages.
English translation of Chinese Second Office Action dated Dec. 21, 2015, corresponding to Chinese Application No. 201410059861.7; 5 pages.
Taiwanese Office Action (with English translation), dated Nov. 3, 2015, corresponding to Taiwanese Application No. 102138934; 16 total pages.
International Preliminary Report on Patentability and Written Opinion of the International Searching Authoirty, corresponding to International Application No. PCT/IB2014/059722, dated Sep. 15, 2015; 9 Pages.
Australian Patent Examination Report 1, dated Sep. 15, 2015, corresponding to Australian Patent Application No. 2014253526; 3 pages.
Eurasian Search Report (with English translation) issued by the Eurasian Patent Organization (EAPO) dated Sep. 16, 2015, corresponding to Eurasian Patent Application No. 201590836; 4 total pages.
Eurasian Search Report (with English translation) issued by the Eurasian Patent Organization (EAPO) dated Sep. 16, 2015, corresponding to Eurasian Patent Application No. 201590835; 4 total pages.
Eurasian Office Action (with English translation), dated May 30, 2016, corresponding to Eurasian Application No. 201590835/28; 4 total pages.
Eurasian Office Action (with English translation), dated May 30, 2016, corresponding to Eurasian Application No. 201590836/28; 4 total pages.
Eurasian Office Action (with English translation), dated Jun. 8, 2016, corresponding to Eurasian Application No. 201390409/28; 4 total pages.
Taiwanese Office Action with English tranlsation of Search Report, dated May 13, 2016, corresponding to Taiwaense Application No. 099131496; 5 total pages.

(56) References Cited

OTHER PUBLICATIONS

Australian Patent Examination Report No. 3, dated Jun. 28, 2016, corresponding to Australian Application No. 2014203364; 3 pages.
English translation of Chinese Third Office Action, dated Jun. 28, 2016, corresponding to Chinese Application No. 201410059861.7; 4 pages.
Korean Office Action (with English translation) dated May 16, 2016, corresponding to Korean Application No. 10-2015-7004820; 10 total pages.
Australian Patent Examination Report No. 1, dated Sep. 21, 2016, corresponding to Australian Application No. 2015243026; 3 pages.
Chilean Office Action (No English translation available), dated Aug. 22, 2016, corresponding to Chilean Patent Application No. 2014-00315; 8 pages.
English translation of Israeli Office Action dated Aug. 30, 2016, corresponding to Israeli Application No. 243627; 2 pages.
Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.
Tolin et al., "Purification and Serology of Peanut Mottle Virus", The American Phytopathological Society, vol. 73, No. 6, 1983; pp. 899-903.
Casas et al., "Detection of enterovirus and hepatitis A virus RNA in mussels (*Mytilus* spp.) by reverse transcriptase-polymerase chain reaction", Journal of Applied Microbiology, vol. 90, 2001; pp. 89-95.
Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 8, Aug. 1988; pp. 1983-1988.
Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.

\* cited by examiner

SEQUENCE LISTING

<160> NUMBER OF SEQ ID NOS: 5

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
tggtggacca tttctaactc ctatagtacc                                        30

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
gttaatagta aacacatgag agcttgtttc                                        30

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
agtgggtatc gctactaacc tacactc                                           27

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
gatctgtcat catccagtct tctatgc                                           27

<210> SEQ ID NO 5
<211> LENGTH: 331
<212> TYPE: DNA
<213> ORGANISM: Artificial Sequence
<220> FEATURE:
<223> OTHER INFORMATION: Synthetic Sequence

<400> SEQUENCE: 5
agtgggtatc gctactaacc tacactcgga aatatgattg cttactactt cctaaataaa       60 aaagaaaga caactgaaag agagcatgga tattatctca gctcagattc tggcttcatg       120
acaaatttct taaagaagg cgagagacac ttagtcagtc acctatttac tgaagcaaat       180
aaacctgaaa ctgtggaaac aacggttact acagctcagg aagccaaaag aggcagaata     240
caaacaaaaa aagaagtaag cataaaatgc acaataagag acttggttaa taaaagatgt     300
actagcatag aagactggat gatgacagat c                                    331

METHOD FOR DETECTING INFECTIOUS PARVOVIRUS IN PHARMACEUTICAL PREPARATIONS This application claims the benefit of U.S. Provisional Application No. 61/034,847, which is hereby incorporated by reference.

FIELD OF THE INVENTION

The present invention provides methods for determining viral infectivity and viral content in an enzyme preparation. In certain embodiments, the invention relates to methods for producing a pharmaceutical pancreatic enzyme composition.

BACKGROUND OF THE INVENTION

Pancreatic exocrine insufficiency is a major consequence of pancreatic diseases (e.g., chronic pancreatitis, cystic fibrosis, severe acute necrotizing pancreatitis, and pancreatic cancer), extrapancreatic diseases such as celiac disease and Crohn's disease, and gastrointestinal and pancreatic surgical resection. Replacement of pancreatic exocrine function is important to avoid malnutrition-related morbidity and mortality. One therapy for pancreatic exocrine insufficiency is the oral administration of pancreatic enzymes to provide the duodenal lumen with sufficient active lipase at the time of gastric emptying of nutrients. Typically these enzymes are administered in the form of enteric-coated mini-microspheres to avoid acid-mediated lipase inactivation and to ensure gastric emptying of enzymes in parallel with nutrients.

Pancreatic enzyme preparations (PEPs) obtained from animal sources have been used in various forms over the past seventy years to partially remedy enzyme deficiency in patients suffering from various pancreatic enzyme deficiency and digestive disorders. PEPs typically contain a combination of at least three enzymes including: lipase, protease, and amylase, which are important in the digestion of fats, protein and sugars. One PEP known as pancrelipase is commercially available in the form of enteric coated capsules which contain up to 35,000 USP units/capsule of pancrelipase (e.g., PANCRECARB® (Digestive Care, Inc.), ULTRASE® (Axcan Scandiphann Inc.), PANCREASE™ (McNeil Pharmaceutical), COTAZYME® (Organon USA, Inc.), and CREON® (Solvay Pharmaceuticals, Inc.)).

Since these enzymes are isolated from animal sources, they are susceptible to being contaminated with genomic copies of porcine parvovirus (PPV). While there are a number of known methods for determining the viral infectivity and viral content of animal derived products, they have many drawbacks. For instance, ultracentrifugation and many extraction methods have limited reproducibility and low detection limits, and cannot be readily scaled up for commercial use. Many of these limitations are due to the nature of animal derived products. The particularly complex nature of PEPs is a major cause for the difficulty in precisely and accurately determining their PPV content.

Therefore, there is a need for reproducible, precise, and efficient methods for determining the PPV content and PPV infectivity of PEPs, such as pancrelipase.

SUMMARY OF THE INVENTION

The present invention provides methods for determining viral infectivity and viral genome content in an enzyme preparation, such as a pancreatic enzyme preparation (PEP). In certain embodiments, the invention relates to detecting infectious porcine parvovirus (PPV) and determining PPV DNA content in PEPS, including pancrelipase preparations.

One embodiment is a method for detecting infectious non-enveloped virus, such as PPV, in an enzyme preparation (e.g., a pancreatic enzyme preparation) by: (a) extracting a sample of the preparation at least two times with chloroform to produce a clarified sample with an upper phase and a lower phase; (b) precipitating an aliquot of the upper phase from step (a) with polyethylene glycol (PEG); (c) suspending the product from step (b) in a buffer; (d) precipitating the product from step (c) with PEG; (e) suspending the product from step (d) in a solution; and (f) removal of excess PEG and fine particles from product (e) by chloroform, this allows (i) in step (e) the suspending in a 10-times smaller volume to increase the overall sensitivity up to 10-fold; and (ii) removes the remaining interfering materials from least diluted steps of the most toxic samples (Table 8); (g) detecting the presence of or measuring the amount of infectious virus in the solution. According to one preferred embodiment, the extraction in step (a) is performed three times with chloroform.

The presence of infectious virus can be determined by an infectivity assay system comprising a detection agent for detecting the virus. Step (f) may include performing nucleic acid amplification on an aliquot from the solution of step (e), and producing an amplification profile that indicates viral content of the preparation. The nucleic acid amplification can be performed by polymerase chain reaction (PCR). Alternatively, the presence of infectious virus can be determined by immunofluorescence, such as with a fluorescence-focus units system comprising a specific detection agent for the virus to distinguish virus-induced cytopathic effects from pancrelipase-related toxic effects.

Detection or measurement of the amount of infectious virus in a dosage form or batch of dosage forms, where each dosage form contains an enzyme preparation (such as a PEP), can be performed by the aforementioned method. In the case of a batch of dosage forms, detection or measurement of the amount of infectious virus can be determined by detecting or measuring the amount of infectious virus in one or more dosage forms selected from the batch.

The enzyme preparation can be a pancreatic enzyme preparation (PEP), e.g., pancrelipase (such as that or porcine origin) or pancreatin. According to a preferred embodiment, the enzyme preparation includes lipase, amylase, and protease.

The presence of infectious virus can be determined by an infectivity assay system comprising a detection agent for detecting the virus.

The nucleic acid amplification can be performed by polymerase chain reaction (PCR).

Another embodiment is a method for evaluating (or validating) a PEP, or a batch of PEPs by: (a) extracting a sample of the PEP (or a sample of a PEP from the batch) at least two times with chloroform producing a clarified sample having an upper phase and a lower phase; (b) precipitating an aliquot of the upper phase from step (a) with polyethylene glycol (PEG); (c) suspending the product from step (b) in a buffer; (d) precipitating the product from step (c) with PEG; e. suspending the product from step (d) in a solution; (f) detecting the presence of or measuring the amount of infectious virus in the solution, and (g) selecting a PEP or batch of PEPs based on the detection or measurement results. A PEP or batch of PEPs may be selected for pharmaceutical use if the amount of infectious virus or viral particles measured is below a threshold level.

A dosage form or batch of dosage forms, where each dosage form contains a PEP, can be evaluated or validated by the aforementioned method. In the case of a batch of dosage forms, the batch can be evaluated or validated by detecting or measuring the amount of infectious virus in one or more dosage forms selected from the batch.

In yet additional embodiments, the invention relates to a method for producing a PEP by any of the aforementioned detection methods.

Yet another embodiment is a method for producing a PEP or a batch of PEPs by (a) obtaining a PEP or batch of PEPs, and (b) (i) detecting or measuring the amount of infectious non-enveloped virus in a sample of the PEP, or one or more samples from one or more of the PEPs in the batch, by the aforementioned detection method, or (ii) validating the PEP or batch of PEPs by the aforementioned validation method. The method can further include the step of (iii) incorporating the PEP or batch of PEPs into one or more dosage forms.

In one embodiment, the PEP or batch of PEPs are validated if the measured viral content is below a threshold level. In the event the PEP or batch of PEPs have a viral content above the threshold level, the PEP or PEPs can be further processed to reduce their viral content and again subject to the validation process.

Yet another embodiment is a method of producing a dosage form or a batch of dosage forms by (a) obtaining a dosage form or batch of dosage forms, each dosage form containing a PEP, and (b) (i) detecting or measuring the amount of infectious non-enveloped virus in the dosage form, or in one or more of the dosage forms in the batch by the aforementioned detection method, or (ii) validating the dosage form or batch of dosage forms by the aforementioned validation method.

Yet another embodiment is a method of controlling steatorrhea in a patient in need thereof, or treating a patient with partial or complete exocrine pancreatic insufficiency by (i) obtaining a pancreatic enzyme preparation, (ii) detecting or measuring the amount of infectious non-enveloped virus in the pancreatic enzyme preparation by the aforementioned detection method, and (iii) administering an effective amount of the pancreatic enzyme preparation to the patient when the infectious load in the pancreatic enzyme preparation are below a threshold level. The pancreatic insufficiency can be that caused by cystic fibrosis (CF), chronic pancreatitis due to alcohol use or other causes, surgery (pancreaticoduodenectomy or Whipple's procedure, with or without Wirsung duct injection, total pancreatectomy), obstruction (pancreatic and biliary duct lithiasis, pancreatic and duodenal neoplasms, ductal stenosis), other pancreatic disease (e.g., hereditary, post traumatic and allograft pancreatitis, hemochromatosis, Shwachman's Syndrome, lipomatosis, and hyperparathyroidism), and poor mixing (Billroth II gastrectomy, other types of gastric bypass surgery, gastrinoma).

DETAILED DESCRIPTION

Figure 1:
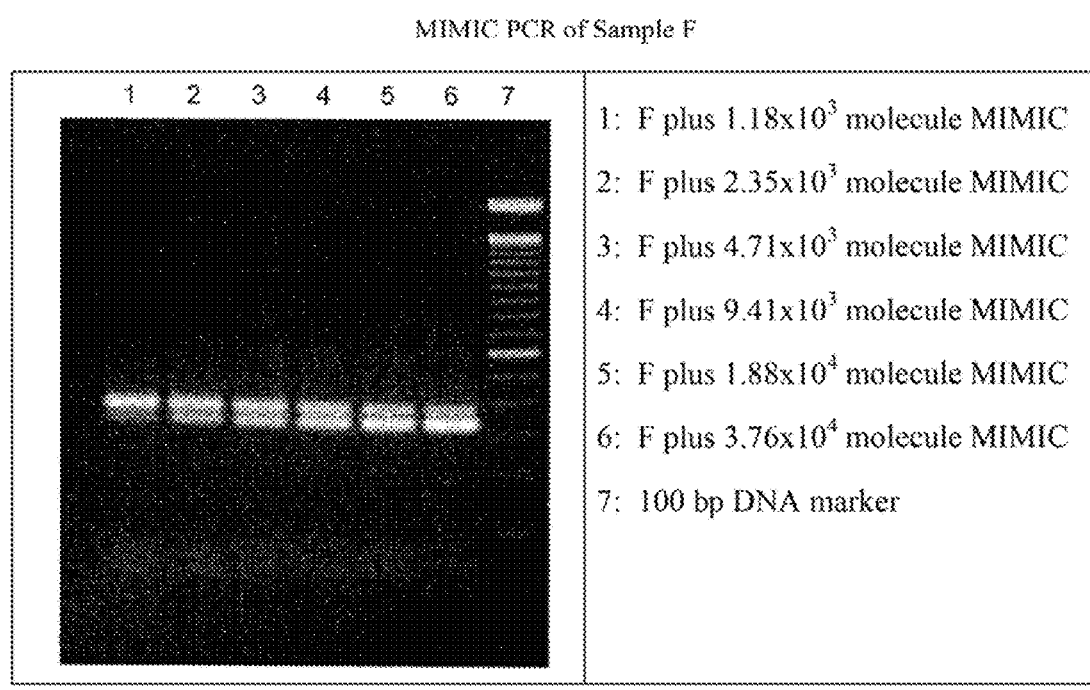
FIG. 1 shows the PPV content analysis of sample F in a quantitative PCR reaction.
Figure 2:
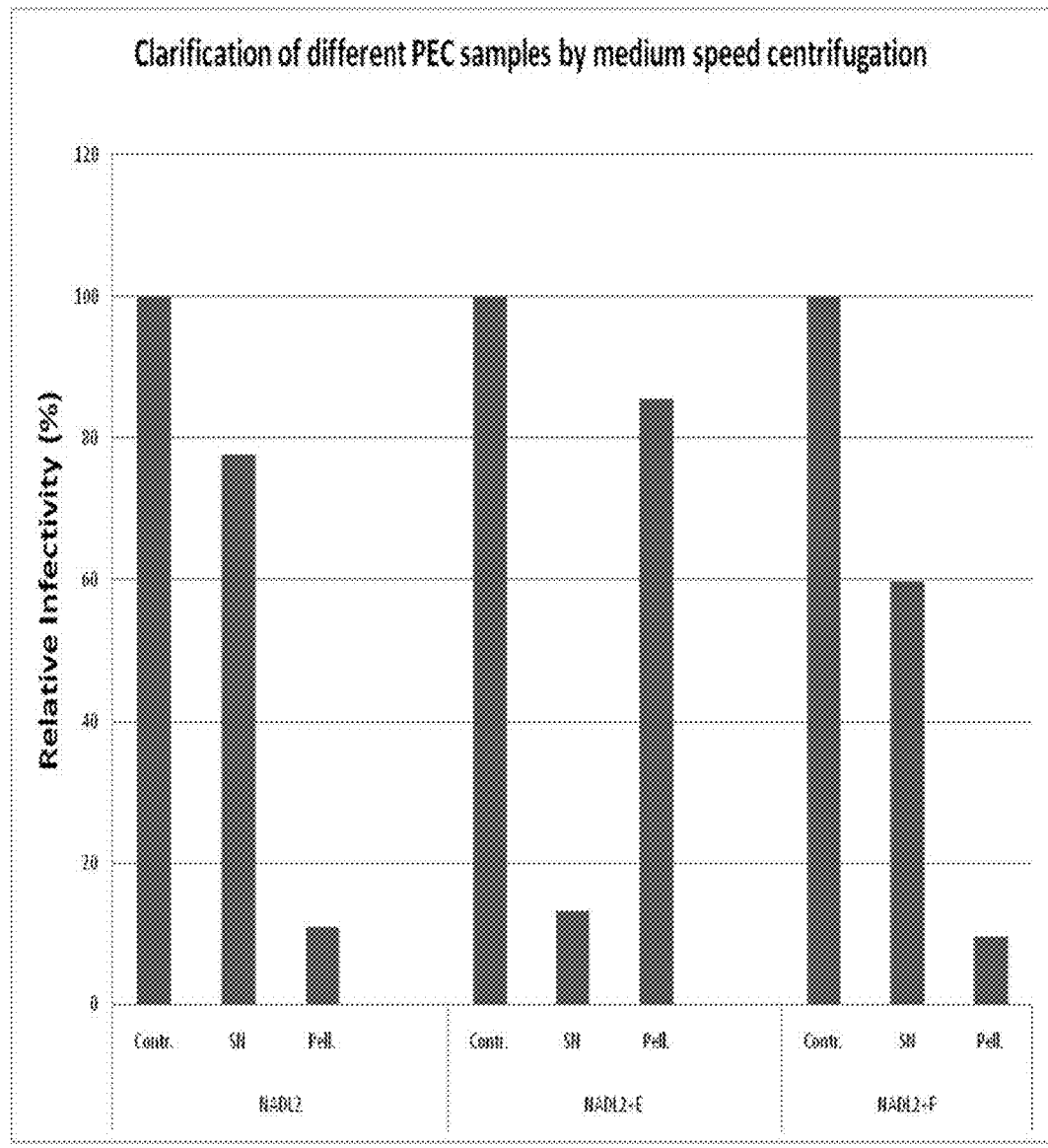
FIG. 2 shows the infectivity of fractions (relative to an initial spiked mix) prepared in Example 1, subsection G.

Pancrelipase preparations contain three major kinds of enzymes: lipase, protease and amylase. The activity of any of these enzymes can be toxic to the cells used for detecting PPVs, and the enzymes may also inhibit PPV infection of the test cell lines in other ways. Other compounds present in the preparations may also interfere with PPV infection. Since cell proliferation is necessary for PPV replication, the presence of any of these cytostatic or toxic enzymes can further reduce the efficiency of viral infection and prevent an accurate determination of infectious virus in PEP samples.

The present inventor here researched methods for clarifying pancrelipase sample so that more precise and reproducible viral content measurements could be obtained. Incubation pancrelipase samples with porcine testis cells (PT, ST (ATCC: CRL-1746) or equivalent) indicated that more than 0.5 mg/mL concentration of dry material is toxic for the cells. Cytostatic effects became negligible under a concentration of 0.1 mg/mL. Reduction of the proteases activity by prolonged storage only reduced the cytotoxicity by a factor of two. Heat inactivation at 65° C. was found to decrease the cytotoxic and cytostatic effects of pancrelipase samples (See sample E and F in Example 1 below), but also resulted in the virus becoming more inactivated in the presence of pancrelipase. Therefore, while heat inactivation and prolonged storage are not optimal, they may be useful to treat samples prior to infectious virus measurement under certain circumstances. These methods could become less reproducible because heat treatment may lead to conformational changes in the capsids and this makes virus more or less susceptible to inactivation by enzymes in pancrelipase extracts.

The present invention provides reproducible and efficient method for determining PPV content and PPV infectivity of PEPs and supplements, including pancrelipase. This method preserves the infectious non-enveloped virus while substantially eliminating the toxic enzyme materials from the PEP samples. This method has significantly greater precision than prior methods.

Active enzymes which may be present in a PEP include, but are not limited to, pancreatic enzymes, such as pancrelipase (a mixture of lipase, proteases, and amylase). Other active enzymes which may be present in PEPs are: active proteases including, but not limited to: trypsin, E.C. (Enzyme Commission Number) 3.4.4.4; chymotrypsin, E.C. 3,4,4,5; chymotrypsin B, E.C. 3,4,5,6; pancreatopeptidase E, E.C. 3.4.4.7; carboxypeptidase A, E.C. 3.4.2.1; and carboxypeptidase B, E.C. 3.4.2.2; active lipases, including, but not limited to: glycerol ester hydrolase (Lipase), E.C. 3.1.1.3; phospholipase $A_2$, E.C. 3.1.1.4; and sterol ester hydrolase, E.C. 3.1.1.13; (III) the nucleases, such as, ribonuclease, E.C. 2.7.7.16 and deoxyribonuclease, E.C. 3.1.4.5; and an active amylase is α-Amylase, E.C. 3.2.1.1.

The enzymes may be available in powder or crystalline form, for example as concentrates of pancreatic enzymes (proteases, amylase, lipase and, in some cases nucleases such as, ribonuclease) derived from animal sources (hog, sheep and bovine). Co-lipase may also be included in the enzyme preparations. PEPs and other enzyme preparations may contain lipase in varying amounts with varying strength, i.e., pancreatin concentrate: 40 USP units per mg of lipase activity or pancreatin concentrate with lipase greater than 100 USP units per mg of lipase activity. It should be understood that, as used herein, the term "enzyme" includes not only the already activated form but also the zymogen precursor which is capable of being transformed into the active form in mammalian intestinal fluid.

In one embodiment, the invention relates to methods for detecting infectious virus particles or infectious virus in PEPs. The infectious virus particles or infectious virus can be of any type including those found in porcine sources. In a preferred embodiment, the methods of the invention detect or measure the amount of porcine parvovirus (PPV) in a PEP sample. PPV is a non-enveloped, small DNA virus (Bergeron et al., Virology, 1993, 197(1):86-98; and *J. Virol.* 1996 April; 70(4): 2508-2515; Simpson et al., *J. Mol. Biol.*, 2002 315(5):1189-98; Szelei et al., 2006. Porcine parvovirus pp. 434-445, in: Parvoviruses (Kerr et al., eds), Hodder Arnold Publ., London, UK) and is the most prominent among the viruses found in PEPs. PPV has a high degree of stability in the environment, and during manufacturing it is resistant to hydrolytic enzymes and relatively high temperature, and remains infective throughout a wide pH range. The method of the invention can also be used to detect or measure the amount of genome copies of other non-enveloped viruses such as EMCV (porcine encephalomyocarditis virus), HEV (swine hepatitis E virus), SVDV (swine vesicular disease virus) and PCV1 and PCV2 (porcine circovirus).

Generally, it is difficult to remove nonenveloped viruses from enzyme preparations during the manufacturing. Therefore, measurement of the presence of nonenveloped viruses, that could potentially be disease-causing, in PEPs is especially important. Clarification or purification of samples with chloroform in the methods of the present invention is an important step before the quantification of PPV. This treatment inactivates the enveloped viruses in the PEP sample. However, most of the nonenveloped viruses survive the chloroform treatment. The inventors have found that this method is also effective for viruses other than PPV, such as nonenveloped RNA viruses.

Definitions

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology. John Wiley and Sons, Inc.: Hoboken, N.J., and *Animal Cell Culture* (Freshney, ed.: 1986).

Common abbreviations correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, and "bp" means base pair(s). "Polymerase chain reaction" is abbreviated PCR; "Reverse transcriptase polymerase chain reaction" is abbreviated RT-PCR; and "Sodium dodecyl sulfate" is abbreviated SDS.

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotides (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid). See *Molecular Biology of the Cell*, Alberts et al., $3^{rd}$ ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/ 0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., 3$^{rd}$ ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO$_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Mammal*, 2$^{nd}$ ed., vol. 2, ch. 9.50, CSH Laboratory Press, 1989; Ausubel et al. (eds.), 1989, *Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

A "therapeutically effective amount" means the amount of a compound or composition that, when administered to an animal for treating a state, disorder or condition, is sufficient to effect such treatment. The "therapeutically effective amount" will vary depending on the compound or composition, the disease and its severity and the age, weight, physical condition and responsiveness of the animal to be treated.

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical formulation such as a dosage form (e.g., a capsule or tablet) comprising at least one active enzyme preparation, in association with a pharmaceutically acceptable excipient, diluent and/or carrier.

The compositions of the invention can be formulated for administration in any convenient way for use in human or veterinary medicine. The invention therefore includes within its scope pharmaceutical compositions comprising a product of the present invention that is adapted for use in human or veterinary medicine.

In a preferred embodiment, the enzyme preparation is conveniently administered as an oral dosage form. Oral dosage forms include tablets, caplets, gelcaps, capsules, and medical foods. Tablets, for example, can be made by compression techniques known in the art, such as wet, dry, or fluidized bed granulation methods.

Suitable pharmaceutically acceptable excipients include, but are not limited to, diluents, binding agents, lubricants, glidants, disintegrants, and coloring agents. Other components such as preservatives, stabilizers, dyes and flavoring agents may be included in the dosage form. Examples of preservatives include sodium benzoate, ascorbic acid and esters of p-hydroxybenzoic acid. Antioxidants and suspending agents may be also included.

Pharmaceutically acceptable excipients, diluents, and carriers for therapeutic use are known in the pharmaceutical art, and are described, for example, in *Remington: The Science and Practice of Pharmacy*, Lippincott Williams & Wilkins (A. R. Gennaro edit. 2005).

As used herein, the term "batch" refers to a group of dosage forms containing an enzyme preparation, such as pancrelipase.

Decreasing Toxicity and Inhibitory Activity from the Pancreatic Enzyme Samples

In order to efficiently assess the amount of the intact PPV genomes and infectious virus particles in a PEP sample, it is preferable to remove as much as possible of the inhibitory and toxic substances from the test portion or aliquot of the PEP sample.

The sample of the enzyme preparation to be tested can be first dissolved in a suitable buffer, such as a weakly alkaline, high capacity extraction buffer. The dissolved sample is preferably subjected to mild agitation to facilitate the extraction of the viruses into the water phase. In one preferred embodiment, a portion or all of the pancreatic enzyme preparation is dissolved in buffer (e.g., an alkaline buffer (such as TrisHCl)), and the solution is mixed for up to about 24 hours, and more preferably up to about 4 hours or 2 hours.

The sample suspension is then clarified by at least two consecutive chloroform extraction steps, preferably using low speed centrifugations, although additional chloroform extractions can be performed if desirable. Preferably, two or three chloroform extractions are performed. Chloroform treatment decreases or eliminates the insoluble particles and the coagulating materials, extracts lipid compounds, and by inactivating the enzyme activities, it reduces the cytotoxic activity of non-viral components that typically interfere with infectivity assays and detection methods.

Following the chloroform treatment, a sample from the upper chloroform clarified layer is further purified by at least two (and preferably only two) polyethylene glycol (PEG) precipitations. Suitable PEG compositions can be utilized for the precipitations. Such suitable PEGs include, but are not limited to PEG 200, PEG 300, PEG 400, PEG 500, PEG 600, PEG 700, PEG 800, PEG 900, PEG 1000, PEG 2000, PEG 3000, PEG 4000, PEG 5000, PEG 6000, PEG 7000, PEG 8000, PEG 9000, PEG 10,000, PEG 11,000, PEG 12,000, PEG 13,000, PEG 14,000, PEG 15,000, PEG 16,000, PEG 17,000, PEG 18,000, PEG 19,000, PEG 20,000, PEG 25,000, PEG 30,000, PEG 35,000, etc. A preferred PEG is PEG 8000.

Before the second PEG precipitation, the precipitates are preferably dissolved in a buffer, such as the extraction buffer. For example, the precipitate can be dissolved in cell culture medium. The remainder of the insoluble material and a portion of the remaining PEG can be removed by another extraction with chloroform.

The methods of the present invention are highly efficient to remove inhibitory substances and typically detect or recover more than 50% of the PPV viruses in the samples, even at extremely low virus titers. Without being bound by any particular theory, the high efficiency of this method is believed to be a result of the unique combination of the protein composition of the pancrelipase samples and the chemical nature of the mild organic solvent and amphiphilic PEG that has low toxicity for infectivity assays. Experiments using other PEG precipitation techniques for viral purification showed that at least 2 to 4 orders of magnitude higher PPV concentrations in the cell culture medium were required for detection than for the method of the present invention.

In developing the present methods, it was determined that the efficiency of precipitation is also significantly higher when the PEG precipitation is carried out on chloroform-treated samples, than on samples clarified with cell culture medium. As a result, other PPV purification techniques require higher centrifugation speeds, which often results in pelleting more contaminating proteins in addition to the virus. The application of ammonium sulfate concentrations, in varying amounts did not result in as efficient virus precipitation unlike in the cases of PPV viral capsid purifications from tissue culture media.

Lower ammonium sulfate concentrations in precipitation steps prior to the PEG precipitations were tested. This resulted in moderately reduced toxicity levels, but there was still a partial loss of virus content by inactivation by the ammonium sulfate. There was a small amount of variability between samples subjected to the same ammonium sulfate/PEG treatment. However, the application of ammonium sulfate treatment is useful under certain conditions for samples as an alternative treatment to the two-step PEG method.

In the methods described herein, 30 different pancrelipase samples have been tested providing quantifiable results for each sample, illustrating that the methods of the present invention are effective for testing various types of pancrelipase samples.

Quantitative PCR

Samples clarified by the chloroform/PEG method as described can also be subjected to PCR assay, such as quantitative PCR assay to determine the amount of viral nucleic acid (e.g., genomic equivalents) present in the sample. The inventors have found that the reproducibility of the quantitative PCR measurements of viral nucleic acid is significantly better when using samples that have been subjected to the chloroform-PEG precipitation method as described above, compared to samples clarified by other techniques.

Application of hot start PCR improved the detection limit for the quantitative PCR reactions. The limit of detection is typically between 5 to 10 genomic equivalents (GE) in one PCR reaction, corresponding to approximately $9\times10^3$ GE/g sample. The present methods using quantitative MIMIC PCR detected approximately 100 PPV molecules in a PCR reaction, which corresponds to approximately $1.25\times10^5$ GE/g sample using the standard volumes of the quantification protocol. Thus, clarification of PEPs using the chloroform-PEG method of the present invention allowed for concentrating the test samples up to 10 times without any significant inhibitory effect on the PCR.

Additionally, in order to detect the presence of longer PPV DNA fragments in the pancrelipase samples, new PCR primer pairs (primers PPVS1 and PPVAS1 below) were designed that are highly specific for the PPV sequences published in the GenBank (NADL-2 has GENBANK ACCESSION NO: NC_001718.1, the Kresse strain has GENBANK ACCESSION NO: U44978.1).

```
Primer PPVS1:
5'-TGGTGGACCATTTCTAACTCCTATAGTACC-3' (SEQ ID NO: 1)

Primer PPVAS1:
5'-GTTAATAGTAAACACATGAGAGCTTGTTTG-3' (SEQ ID NO: 2)
```

This primer pair is especially useful because it covers the allotropic determinant containing VP region, and allows them to differentiate between vaccine (1006 bp allotropic determinant—NADL-2) and wild type PPV strains (879 bp allotropic determinant—Kresse strain). The limit of detection for this primer pair is between about 20 to 50 copies in one PCR reaction.

Development of a Quantitative Infectivity Assay

Infectivity assays preferably utilize cell cultures growing in tissue culture wells, to which a sample is applied. After the chloroform-PEG treatment, the samples can be dissolved in cell culture medium in a volume that is equal to or less than the original sample volume in order to preserve the sensitivity of the infectivity assay. After elimination of traces of chloroform from these solutions by evaporation, direct addition of aliquots of these purified samples to the tissue culture wells, did not noticeably affect the viability and growth rate of the cells in the majority of cases. The results obtained using the methods of the present invention indicate that the level of cytostatic and cytotoxic substances from PEP preparations was reduced at least by one hundred times when compared with untreated samples. An additional benefit of this improved sample purification allows for prolonged incubation of the test cells with the purified samples containing the viral extracts. The increased incubation times result in improved sensitivity of the infectious virus detection method. In one embodiment, the infectivity assay is modified so that the purified virus containing extracts of PEPs are serially diluted (usually 1:4 in each step) in cell culture medium.

In one convenient embodiment, two pancrelipase samples can be tested by the method on one 96-well plate, with the positive controls incubated on another parallel plate. After the fixation of the cells by paraformaldehyde, the presence of PPV virus infection is monitored in each well by the anti-PPV antibody using a standard immunofluorescent assay. The number of all wells that contain positively stained cells are recorded in a table. Fluorescence Focus Infectious Doses ($FFID_{50}$) are calculated according to the Karber formula: $FFID_{50}=10(D-0.5d+d(S))$; where $D=\log_{10}$ of the highest dilution demonstrating 100% infection, $d=\log_{10}$ of the dilution factor and S=the ratio of the total number of wells with infection to the number of wells per dilution. All data are recalculated for 1-gram dry pancrelipase sample after the consideration of processed sample volumes and dilutions. Considering the 0.1 mL titration sample volume and 100 mg/mL sample concentration, the limit of quantification for this particular method, is approximately 200 infectious particles for one-gram original dry PEP. This is believed to be the lowest concentration of virus that can be quantitatively measured by assays of the present invention, for samples lacking any appreciable inhibitory materials. In certain embodiments, the assay is repeated several times using the six parallel wells to quantify the level of infectious viruses.

The effectiveness of the present infectivity assay was compared to the conventional assays using a wild type PPV strain, the Kresse strain. The results showed the methods of the present invention are more sensitive than traditional one-day assays, because the longer incubation time of at least 5 days increased the sensitivity by at least 40 times. The longer incubation time was facilitated by the elimination of interfering and cytotoxic components from the sample using the chloroform-PEG sample extraction/purification methods of the present methods. The immunofluorescence analysis used in the $FFID_{50}$ method also contributes to decreasing false positives (derived from toxicity) that could have been picked up by the $TCID_{50}$ assay. Generally, the $FFID_{50}$ method has been shown to be 2-5 times more sensitive than the $TCID_{50}$ assay (see Table 9), however, if all conditions are optimized (eg, high input of PPV, nonconfluency of cells, a less toxic batch of PEC, etc), the $TCID_{50}$ can approach the $FFID_{50}$ results.

The infectivity assay was modified in a way that the purified virus containing extracts of PEPs were serially diluted (usually 1:4 in each step) in cell culture medium. Diluted samples (100 μL) are added to the subconfluent cells growing on 96-well plates. Altogether, 8 different dilutions (ranging from 1:1 to 1:16384) of the same sample (in 6 parallel series) can be added to a plate and the cells are incubated for at least 5 days at 37° C. in the 5% $CO_2$ containing cell culture.

The present methods have been shown to be especially useful for detecting infectious PPV and for providing purified samples for PCR allowing for PPV nucleic acid quantification in PEPs. It is noted that the present methods can be used generally as a protocol for the detection of potential disease-causing viruses in any preparation for use in pharmaceutical compositions and could represent a very valuable tool for products quality improvement.

In particular the present methods can be used to test an enzyme preparation and to determine the amount of infectious virus in the enzyme preparation such that the enzyme preparation can be used for further manufacture into batch pharmaceutical products. In certain embodiments, an enzyme preparation with an undesirable level of PPV can be identified and further processed for better purity and utilized after further testing.

Samples that contain infectious virus and/or viral amounts detected by nucleic acid amplification above the threshold level could be further processed by inactivation by gamma irradiation or by chemical inactivating agents for use in a final pharmaceutical product. Activated paramagnetic beads are on option for carrying out inactivation of virus in these samples. Samples having more than $10^8$ GE/g should be tested for PPV infectivity. The threshold level of infectious PPV viruses is about $10^5$ $FFID_{50}$ that corresponds to about $10^{4.5}$ $TCID_{50}$.

Example 1

Initial Sample Treatments and PCR Standardizations

A. Sample Materials

All of the tested samples were packaged in their appropriate medical dosage forms. For experiments, aliquots of these samples were suspended at a concentration of 100 mg dry content per ml, in a specific buffer (100 mM Tris/HCl, pH=8.5). During this study, six different products were used for analysis as indicated on Table 1 and listed below as samples A-F.

Samples

A: Pellets

B: Pellets

C: pellets,

D: powder

E: tablet

F: minitablets

1. Handling of Sample Materials

Vials with the original material were stored at room temperature. Before experiments, aliquots of the samples were suspended at a concentration of 100 mg dry content per mL in a specific buffer (100 mM Tris/HCl, pH=8.5). Suspended samples were kept at room temperature for overnight and later they were stored at 4° C.

B. Methods and Reaction Materials

MIMIC PCR protocol, performed according to manufacturer's instructions; however it was optimized for the Hybaid PCR machine and the specific brand of TAQ polymerase.

1. Addition of the following components into the PCR tube:

| | |
|---|---|
| Distilled water | 31.7 μL |
| 10X PCR buffer | 5.0 μL |
| $MgCl_2$ stock (25 mM) | 4.0 μL |
| dNTP (10 mM) | 1.0 μL |
| Forward primer (50 μM) | 1.0 μL |
| Reverse primer (50 μM) | 1.0 μL |
| MIMIC DNA (diluted) | 5.0 μL |
| Template DNA (sample) | 1.0 μL |
| FastStart Taq polymerase (5 U/μl) | 0.3 μL |

2. Amplification:

a. Hot start (95° C. for 5 min)

b. 35 cycles:

denaturing (95° C. for 30 s)

annealing (52° C. for 30 s)

polymerization (72° C. for 2 min)

c. Extension (72° C. for 9 min)

3. Analysis of 10 μL PCR product on agarose gel

TABLE 1

Description of analyzed samples

| Sample | Description |
|---|---|
| A | Pellets VR |
| B | pellets |
| C | pellets, (dry heated) |

TABLE 1-continued Description of analyzed samples

| Sample | Description |
|---|---|
| D | powder |
| E | tablets |
| F | minitablets |

As shown in Table 1, six products with different characteristics were used to test PPV DNA contamination and cytotoxicity.

C. MIMIC PCR of Sample F

FIG. 1 is an agarose gel showing the PPV content analysis of the minitablets (F) sample. Increasing amounts of MIMIC DNA (smaller size) gradually compete out the PPV DNA isolated from sample F. The amount of MIMIC DNA necessary to get the same density of the DNA bands after amplification indicates the concentration of PPV DNA in the sample. Values are adjusted by the ratio of the size of the two fragments (331 bp and 372 bp).

Standard Measurement of PPV DNA Content in the Samples

Viral DNA was isolated from each sample using a silica gel based method. Usually, 200 µl suspension of a sample was used for one preparation and 50 µL DNA solution was obtained. This sample was stored at 4° C. PPV genomic DNA content was determined by MIMIC PCR. In the first step, PPV content was estimated by amplification of the virus DNA from different dilutions of the sample. In the next step, a certain dilution of the sample, which gave the appropriate amplified amount of DNA for detection on agarose gel was compared to a ten times dilution series of the MIMIC DNA stock. According to the result of the first MIMIC PCR, the MIMIC DNA stock was diluted five times again with a scale factor of two in the range of the estimated concentration of the sample DNA. After scanning the result of the MIMIC PCR from an agarose gel run, comparison of the densities of test sample bands and MIMIC bands provide a method for calculating the amount of viral DNA in the sample.

D. Calculation of DNA Content by MIMIC PCR

All samples except sample D contained a similar amount of PPV DNA as identified by quantitative PCR. Sample DNA's were originally diluted five times and MIMIC DNA was diluted two times in every step of the dilution series. For sample D, higher dilution of MIMIC DNA was required to measure the PPV DNA content.

Analysis of the Viral DNA Content by MIMIC PCR

Summary of result indicates that one tablet or one dose of pancreatine products could contain at least 107 PPV particles except the powder (sample D) that has 10 times less.

Dry sample materials were dissolved slowly, first with continuous and later sporadic mixing at room temperature. The goal was to obtain a high-concentration solution (100 mg/mL) because the identification of a low-level of virus requires high amounts of test material. After overnight incubation, samples could be easily processed in smaller volumes because they became completely dissolved. For longer time they can be stored at 4° C., however, in this case aggregates could arise especially in the case of E and F samples. Usually, vigorous mixing with a pipette enables us to get a uniform suspension. This was important, because viral material could bind to the larger particles, which may lead to varying results during the tests for the measurement of the virus.

Purified DNA was used for the quantification of the virus because the high protein content made it difficult to do PCR on PPV DNA template directly on the samples. During the preliminary tests, the silica gel-based methods proved superior to the classical proteinase-K/phenol-chloroform method for the isolation of clean viral DNA from the pancrelipase products. Besides producing higher yields, less inhibition was observed during the PCR analysis. Undiluted and less than 10 times diluted DNA samples were used to obtain satisfactory amplification for the MIMIC assay. Samples A-C and E-F contained higher amount of PPV DNA, while sample D was less contaminated, therefore one magnitude less MIMIC DNA was required for this sample. Computation of the data obtained from scanning the MIMIC PCRs showed that there were at least $10^7$ genomic viral DNA in one gram of most samples. Only the D sample contained one magnitude less PPV, while E and F samples were close to the 108 levels.

F. Cytotoxic and Cytostatic Effect of Different Samples

TABLE 2

Cytotoxic and cytostatic effect of different samples

| | PT CELLS | | | | | | | |
|---|---|---|---|---|---|---|---|---|
| | 10x dilution | | 100X dilution | | 400x dilution | | 1000x dilution | |
| Samples | High density | Low density | High density | Low density | High density | Low density | High density | Low density |
| 24 hours incubation | | | | | | | | |
| A | 8/8 | 8/8 | 8/8 | 8/8 | 0/6 | 0/6 | 0/6 | 0/6 |
| B | 8/8 | 8/8 | 8/8 | 8/8 | 0/6 | 0/6 | 0/6 | 0/6 |
| C | 8/8 | 8/8 | 8/8 | 8/8 | 0/6 | 0/6 | 0/6 | 0/6 |
| D | 8/8 | 8/8 | 3/8 | 8/8 | 0/6 | 0/6 | 0/6 | 0/6 |
| E | 8/8 | 8/8 | 2/8 | 6/8 | 0/6 | 0/6 | 0/6 | 0/6 |
| F | 8/8 | 8/8 | 4/8 | 8/8 | 0/6 | 0/6 | 0/6 | 0/6 |
| 48 hours incubation | | | | | | | | |
| A | 8/8 | 8/8 | 8/8 | 8/8 | 0/6 | 2/6 | 0/6 | 0/6 |
| B | 8/8 | 8/8 | 8/8 | 8/8 | 0/6 | 2/6 | 0/6 | 0/6 |
| C | 8/8 | 8/8 | 8/8 | 8/8 | 0/6 | 1/6 | 0/6 | 0/6 |

TABLE 2-continued

Cytotoxic and cytostatic effect of different samples

PT CELLS

| Samples | 10x dilution | | 100X dilution | | 400x dilution | | 1000x dilution | |
|---|---|---|---|---|---|---|---|---|
| | High density | Low density | High density | Low density | High density | Low density | High density | Low density |
| D | 8/8 | 8/8 | 4/8 | 8/8 | 0/6 | 2/6 | 0/6 | 0/6 |
| E | 8/8 | 8/8 | 2/8 | 8/8 | 0/6 | 0/6 | 0/6 | 0/6 |
| F | 8/8 | 8/8 | 6/8 | 8/8 | 0/6 | 2/6 | 0/6 | 0/6 |
| *4 days incubation* | | | | | | | | |
| A | 8/8 | 8/8 | 8/8 | 8/8 | 0/6 | 3/6 | 0/6 | 0/6 |
| B | 8/8 | 8/8 | 8/8 | 8/8 | 0/6 | 3/6 | 0/6 | 0/6 |
| C | 8/8 | 8/8 | 8/8 | 8/8 | 0/6 | 1/6 | 0/6 | 0/6 |
| D | 8/8 | 8/8 | 8/8 | 8/8 | 0/6 | 3/6 | 0/6 | 0/6 |
| E | 8/8 | 8/8 | 6/8 | 8/8 | 0/6 | 2/6 | 0/6 | 1/6 |
| F | 8/8 | 8/8 | 8/8 | 8/8 | 0/6 | 5/6 | 0/6 | 2/6 |

Analysis of the samples indicated that they contain high protease activity. Ten times dilution of all samples removed almost all of the cells from the wells (Table 2). Results were recorded after 24 hours; however, this phenomenon partially could be observed immediately 1-4 hours after the addition of the samples. Usually, 3 hours later at least 40% of the cells were floating. The number of rounded and floating cells were less when 100 hundred times dilution of the samples was used. However, monitoring the cells at different times, most of the wells contained dying cells after 4 days and the number of cells did not increased in those wells, which were received initially lower amount of cells. At higher dilutions of the samples, mainly cytostatic effects were observed in the case of some low density well. (20-30% initial cell density). Cells at high concentrations very well tolerated the 400 and 1000 times dilutions.

This assay was repeated again with high density of cells, but plates with 10 and 100 times sample dilution were harvested after 24 hours and plates with 400 and 1000 dilutions were harvested after 4 days. There was no PPV infected cell on any of the plates.

Longer storage at 4° C. reduces somewhat the toxicity of the samples. Samples E and F were tested after 10 and 21 days of storage and it was found that in both cases 20-50% of the cells survived the 24 hr incubation period when 10 times diluted samples were used. One hundred times dilution of the E samples resulted in no cell killing but at 20 and 50 times dilutions, cytopatic effects were observed. F sample remained more toxic; all investigated wells contained dying cells after 24 hours when 100 times diluted samples were used. Spiking of the 21 days old samples with NADL-2 or Kresse purified virus, there was a reduction in efficiency of viral infection. Infectivity could not be determined accurately with samples in the 10 times dilution wells because of the cell death, but at least one magnitude of reduction could be observed. Wells containing the 100 times dilution F sample material showed 55% of the control level of infection for both virus strains. The reduction levels in wells with 100 times diluted E sample gave 61.5% for Kresse and 63.0% for NADL-2. At 1000 times dilution, all samples gave similar results to the control.

Table 2 shows that there was a significant amount of cytotoxic and cytostatic activity in the pancreatic enzyme products. One day after the suspension of the dry material, 10 times dilution of the 100 mg/mL stock suspensions has a high protease activity in the case of all samples. Cytotoxic and cytostatic effects were noticed at 100 times dilution. Mainly cytostatic effect could be observed at 400 and 1000 times dilutions when lower amount of cells were plated (20-30% density).

G. Clarification Experiments

Purified NADL-2 virus was diluted before the centrifugation at 1 to 10 ratios into cell culture medium, and suspension of E and F samples. After elaborate mixing, debris from the one ml aliquot of medium and pancrelipase products was removed by medium speed centrifugation (14 000 g, room temperature, 10 minutes). Supernatant was transferred into clean tubes and the pellet was resuspended in the same volume as the original sample. Infectivity of the fractions was determined and the relative infectivity was expressed in relation to the initial spiked mix. The results are shown in FIG. 2. Addition of E sample facilitated pelleting the virus, while F sample did not influence significantly the sedimentation.

1. Heat Inactivation Experiments

The preliminary experiments with highly purified and trypsin digested PPV indicated that these virus stocks were more sensitive to the effect of heat than it was published previously. Therefore, freshly prepared virus stocks were used to determine the effect of pancrelipase products on the heat inactivation of PPV virus. Virus was added to the cell culture medium and the suspension of E and F samples at a ratio of one to ten. After careful mixing 100 μL aliquots were transferred into clean tubes and the samples were transferred to the appropriate temperatures. After a one-hour incubation the samples were transferred to 4° C. for an overnight storage. Before the infectivity assay, samples were initially diluted with 1.9 mL cell culture medium. Results of the virus titration were expressed in relation to the appropriate control samples, which were incubated at room temperature (Table 3). Pancrelipase products significantly reduced the infectivity of both NADL-2 and Kresse, although different virus stocks displayed different levels of heat inactivation. F sample was more inhibitory for the viral activity than E sample (Table 3). Prolonged incubation of the heat-inactivated samples with PT cells was also performed along with the infectivity assays. A reduction of cytotoxicity was observed beginning at 55° C., and it was greatly reduced at 65° C. However, cytostatic effect of the 100 times diluted sample remained high, even at 65° C.

TABLE 3

Heat inactivation of the PPV virus Strain NADL-2 and Kresse

| Sample | NADL-2 | | | | Kresse | | | |
|---|---|---|---|---|---|---|---|---|
| | RT | 45° C. | 55° C. | 65° C. | RT | 45° C. | 55° C. | 65° C. |
| K | 100 | 77.2 | 80.6 | 48.9 | 100 | 61.7 | 74.4 | 19.7 |
|   | 100 | 62.8 | 56.8 | 21.7 | 100 | 65.6 | 30.9 | 1.75 |
| E | 108.6 | 95.2 | 3.73 | 0.37 | 59.2 | 39.2 | 1.40 | <0.01 |
|   | 84.5 | 96.7 | 1.28 | 0.14 | 45.4 | 25.3 | 0.27 | <0.01 |
| F | 97.8 | 35.8 | 0.37 | <0.01 | 12.1 | 1.98 | 0.21 | <0.01 |
|   | 47.8 | 9.60 | 0.21 | <0.01 | 5.81 | 0.94 | <0.01 | <0.01 |

Table 3 shows that one-hour treatment of the spiked virus at increasing temperatures resulted in significant inactivation in the presence of pancreatic products in comparison with dilution in tissue culture medium. Two separate experiments were done on two different stocks of NADL-2 and Kresse strains. The relative infectivity of the viruses was expressed in comparison to control (K) samples treated at room temperature (RT).

J. Titration of PPV and the Cytoxicity Assay

During the spiking experiments, both the vaccine (NADL-2) and the wild type (Kresse) strains of PPV were used. Viruses were produced in porcine testis (PT) cells and they were either immediately stored after the lysis of cells or went through a procedure resulting in purified stocks. PT cells were seeded on 96 well tissue culture plates ($2\times10^4$ cells in 100 µL medium per well) to reach an approximately 80-90% confluence after overnight incubation. Samples were diluted in complete cell culture medium using intensive mixing. Samples were added to wells in 100 µL volumes and the assay was done in three parallels. Depending on the PPV strain, cells were fixed with formaldehyde either 20-24 hours (NADL-2) or 22-26 hours (Kresse) after infection. Mouse monoclonal anti-PPV antibody and FITC-labeled anti-mouse secondary antibody was used to identify the infected cells. Fluorescent focuses (ffu) were read by using fluorescent microscopy. Usually, those wells were counted in the dilution series that contained more than 20 but less than 100 infected cells.

Cytotoxicity assays were done similarly as the titration experiments. However, cells were plated at different densities to be able to monitor changes for longer time and observe cytostatic effects also. Changes in the number of living cells were monitored by eye observation using light microscopy.

Example 2

Two-Step PEG Precipitations

Polyethylene glycols (PEG) with different molecular weight (PEG3400, PEG8000 and PEG20000) were used to test the virus precipitation. PEG 8000 gave the best result because there was no detectable virus either in the first or in the second upper phase. PEG 3400 and PEG 20000 were less effective, since in their upper phase virus DNA could be detected by PCR.

In each case 1 mL 20% PEG, 300 mM NaCl, 100 mM Tris/HCl pH=8 was mixed with 1 mL of the sample (100 mg/mL). All samples were incubated on ice for 1 hour and centrifuged at 14,000 g for 5 min. The supernatant was removed and the pellet was dissolved in 1 mL 100 mM Tris/HCl, pH=8. An 100 µL aliquot of the resolved pellet was stored for DNA preparation and the remaining 900 µL was reprecipitated with 900 µL PEG solution (20% PEG, 300 mM NaCl, 100 mM Tris/HCl pH=8) incubated on ice for 1 hour and centrifuged at 14,000 g for 5 min. The supernatant was again removed and the pellet was dissolved in 900 µL 100 mM Tris/HCl pH=8. DNA was prepared from each precipitation step (100 µL first precipitate, 200 µL first upper phase, 100 µL second precipitate, 200 µL second upper phase) representing 100 µL aliquots of the original sample. The DNA samples were dissolved in 50 µL water and 2 µL was used for PCR.

Example 3

Three-Step Precipitations

A three-step precipitations were also performed, for these reactions, 1 mL of sample was first incubated on ice with 200 µL ammonium sulfate (($NH_4$)$_2SO_4$) for 1 hour and then centrifuged at 14,000 g 5 min. The supernatant was removed and the pellet was dissolved in 1 mL 100 mM Tris/HCl pH=8. Next, a 900 µL aliquot of the ammonium sulfate supernatant was reprecipitated with 900 µL PEG solution, incubated on ice for 1 hour and centrifuged at 14,000 g (5 min). The supernatant was removed and the pellet was dissolved in 750 µL 100 mM Tris/HCl pH=8. In the third step, a 100 µL aliquot of the dissolved pellet was taken for DNA preparation and the remaining 650 µL was reprecipitated with 650 µL PEG solution, incubated on ice for 1 hour and centrifuged at 14,000 g for 5 min. The supernatant was then removed and the pellet was redissolved in 650 µL 100 mM Tris/HCl pH=8.

The $(NH_4)_2SO_4$ precipitation resulted in a thick pellet, which contained detectable amount of viral DNA though the majority of the viral DNA remained in the supernatant. The $(NH_4)_2SO_4$ also had an influence on the PEG precipitation, making it less effective since a noticeable amount of virus DNA remained in the $(NH_4)_2SO_4$ containing supernatant.

In an effort to evaluate the three-step precipitation with $(NH_4)_2SO_4$, the effect of $(NH_4)_2SO_4$ and NaCl concentration on the three-step virus precipitation was studied. First, ammonium sulfate precipitations were performed using different concentrations of $(NH_4)_2SO_4$ in the presence of some NaCl. One ml aliquots of pancrelipase sample (100 mM Tris/HCl pH=8) were adjusted to contain 20% $(NH_4)_2SO_4$ and 150 mM NaCl; 15% $(H_4)_2SO_4$ and 150 mM NaCl; 10% $(NH_4)_2SO_4$ and 150 mM NaCl; 20% $(NH_4)_2SO_4$ with 300 mM NaCl. Samples were incubated on ice with for 1 hour and the precipitate was centrifuged at 14,000 g for 5 min. The supernatant was removed and the pellet was dissolved in 1 mL 100 mM Tris/HCl pH=8. In every case, the majority of the virus remained in the supernatant, however the higher the ammonium sulfate concentration, the more viruses remained in the precipitate. The $(NH_4)_2SO_4$ also had a concentration-dependent influence on the PEG precipitation, the higher the $(NH_4)_2SO_4$ concentration the more viruses stay in the supernatant. The initial $(NH_4)_2SO_4$ has (naturally) a very limited effect on the second PEG precipitation. The effect of NaCl concentration on the first step $(NH_4)_2SO_4$ precipitation was also studied. NaCl did not have any significant difference on the amount of the ammonium sulfate-precipitated virus.

Example 4

Comparison of Toxicity and Viral Infections from Differently Processed Samples

A. Toxicity Tests

The toxicity and the viral infectivity of differently prepared samples were analyzed. Samples were prepared (3 duplicates from each) from enzyme samples that had undergone one PEG precipitation, two PEG precipitations, and a three-step precipitation (ammonium sulfate precipitation followed by two PEG precipitations). An untreated sample served as a control. All of the treated samples were dissolved in cell culture medium. There were no significant differences in the viral DNA concentration among samples; even samples prepared with the three-step precipitation method contained around 70% of the original viral DNA load. Different volumes (200 µL, 100 µL 50 µL and 25 µL) from all samples were added to a well containing adherent PT cells in 70 µL medium on a 96 well plate. There was no toxicity detected in the three-step and the twice PEG precipitated Pancreatin-powder samples (Table 4). All the non-toxic samples tested negative for virus in tissue culture after three days incubation.

TABLE 4

Comparison of toxicity and vial infections from differently processed samples

| | | Toxicity on cell | | | |
|---|---|---|---|---|---|
| | GC/ml | 200 µL/well | 100 µL/well | 50 µL/well | 25 µL/well |
| 1 PEG | 2.88E+07 | + | + | + | − |
| | 3.06E+07 | + | + | + | − |
| | 2.99E+07 | + | + | + | − |
| 2 PEG | 4.17E+07 | − | − | − | − |
| | 1.99E+07 | − | − | − | − |
| | 2.70E+07 | − | − | − | − |
| 3 step | 1.91E+07 | − | − | − | − |
| | 1.89E+07 | − | − | − | − |
| | 1.85E+07 | − | − | − | − |
| Untreated control | 2.44E+07 | NA | NA | NA | NA |
| | 2.47E+07 | NA | NA | NA | NA |
| | 2.88E+07 | NA | NA | NA | NA |

B. Viral Spiking Tests

To test the effect of PEG precipitation on the viral infectivity we spiked three 1 mL aliquots of the pancrelipase sample with around 25 infectious units (FFU) of the virus (PPV NADL-2 strain). The spiked samples were precipitated twice with PEG the precipitates were resolved in 1 mL tissue culture medium and aliquots (200 µL, 100 µL 50 µL and 25 µL) were plated as previously on 96 well plate. As a control, 1 mL spiked tissue culture medium was used. There was no significant difference in the infectivity between the PEG precipitated viruses from the samples and the tissue culture diluted viruses (Table 5), proving that the PEG precipitation is nearly 100% effective in eliminating the undesirable toxic enzymes and contaminants while at the same time the PEG does not have any effect on the viral infectivity.

TABLE 5

Effect of PEG precipitation on the viral infectivity of PPV NADL-2 and PPV NADL-2 spiked pancrelipase samples precipitated twice with PEG.

| | | Virus titer ffu | | | |
|---|---|---|---|---|---|
| | | 200 µL/well | 100 µL/well | 50 µL/well | 25 µL/well |
| Spiked sample | Sample 1 | 5 | 4 | 0 | 2 |
| | Sample 2 | 7 | 7 | 2 | 0 |
| | Sample 3 | 4 | 6 | 0 | 2 |
| Diluted virus | Control 1 | 4 | 2 | 3 | 1 |
| | Control 2 | 7 | 2 | 4 | 2 |
| | Control 3 | 4 | 3 | 2 | 3 |

Samples for individual tests were suspended at a concentration higher than 100 mg dry content per mL, in the solution buffer (100 mM Tris/HCl, pH=8.0). Suspended samples were kept at room temperature for overnight and later the volume was adjusted to reach the final concentration (100 mg/mL; usually in 40 mL).

The previously described chloroform extraction method was modified to accommodate the increased test volumes. Samples were cleared up by three consecutive chloroform extractions using 10, 12 and 15 mL chloroform to treat the initially 40 mL pancreatin material. Sample was mixed with chloroform inverting the tube at least ten times and then letting it stand for one hour at 12-18° C. Before centrifugation, the sample was mixed again and the phase separation was performed by one-hour centrifugation at 2000 g. After the last chloroform extraction, the sample was allowed to stand for one day at 12-18° C. and centrifuged again to remove the remaining chloroform and the developing turbidity. The clear supernatant was transferred into a new tube and it was used for the consecutive experiments.

Because the clear supernatant still develops turbidity after a prolonged storage, three samples were tested for the effect of the removal of this additional precipitate. One sample was incubated for 47 days, a second sample was incubated for 14 days and a third sample was incubated for one day at RT and the turbidity was removed by centrifugation (one hour at 4° C., using 2000 g). As a control, untreated freshly prepared sample was used. There were no significant differences among samples prepared over the course of these different times; however, the even the longer incubation resulted in more pellet and cleaner sample. (Table 6).

TABLE 6

Effect of incubation time on the removal of turbidity

| Incubation time (days) | GC/mL |
|---|---|
| 47 | 2.28E+07 |
| | 2.15E+07 |
| 14 | 2.14E+07 |
| | 2.32E+07 |
| 1 | 2.51E+07 |
| | 3.79E+07 |
| Fresh | 2.32E+07 |
| | 2.12E+07 |

Example 5

Determination of PPV Infectivity of Pancrelipase Compositions Using Purified Samples A. Samples Utilized
Powder and minitab Pancrelipase samples
B. Abbreviations
FFU: Fluorescent focus unit. A positive FFU indicates an infected cell, that typically has viral antigens in the cell nucleus about 24 hrs after infection. The presence of the viral antigens in the cell nucleus can be shown by immunofluorescence, typically by using a fluorescently tagged antibody to one of the viral antigens, and detecting the fluorescence in the cell nucleus (as described in Dev. Cell, Vol. 1, p. 297, 2001, which is hereby incorporated by reference in its entirety).
C. Instruments and Equipment
96-well cell culture cluster, Corning 3595;
24-well cell culture cluster, Corning 3524;
Tissue-culture flask, Corning T75, 430641;
2 ml polypropylene centrifuge tubes (Sarstcdt, cat. 72.695);
Fluorescence Microscope equipped with a Mercury lamp 100 W, type 307.072.057 and with a 488 nm filter.
D. Reagents and Solutions
SOLUTION A: PBS stock solution: invitrogen cat. 14190-144.
SOLUTION B: EDTA 100× stock solution: 5 g EDTA in 50 mL of purified water.
SOLUTION C: Trypsin 100× stock solution: 1% Trypsin in 50 mL in PBS.
SOLUTION D: Trypsin 1× solution: 0.01% Trypsin+ 0.04% EDTA.
SOLUTION E: TRIS-HCl 100 mM, pH 8.
SOLUTION F: PEG 8000 20%, 300 mM sodium chloride.
SOLUTION G: Dulbecco's modified Eagle's medium with high glucose (Invitrogen cat. 11965-092) supplemented with Penicillin 100 IU per mL, streptomycin 50 ug per mL and 6% fetal bovine serum (Hyclone, certified Australian). Modified from Journal of Virology, vol. 70, p. 2508-2515, April 1996, which is incorporated herein by reference in its entirety.
SOLUTION H: 3% formaldehyde in solution A.
SOLUTION I: 3% Triton X 100, 0.1% BSA and 0.05% Tween 20 in solution A.
SOLUTION J: 0.1% BSA and 0.05% Tween 20 in solution A.
Porcine testis cells (PT cells) cloned from swine testis (ST) as described in Journal of Virology, vol. 70, p. 2508-2515, April 1996 (which is incorporated herein by reference in its entirety), were used as the cells for cell culture to determine viral infectivity.
E. Methods
1. Cell Culture
Cells are grown in solution G at 37° C. 5% $CO_2$. The cell cultures are split every 3-4 days using Trypsin solution A at a ratio of 1 in 3.
Cells are transferred to a 96-well plate ($10^5$ cells per well) and grown at 37° C./5% $CO_2$. They are ready to be infected when they are semi-confluent.
2. Sample Preparation
4 g of pancrelipase sample was dissolved in less than 40 mL of solution E and agitated overnight. The volume was adjusted to 40 mL (forming sample suspension). 40 mL of suspension was extracted with 10 mL chloroform in a 50 mL polypropylene tube and centrifuged at 2000 g for 30 min at 4° C. The upper phase which contains the sample was removed and the chloroform extraction was repeated twice more. The last extraction was left at 4° C. for 1 day before centrifugation to remove additional turbidity.
3. Virus Precipitation
1 mL of solution F is added to one ml of sample, followed by mixing and incubation on ice for 1 h. This mixture is centrifuged at 1000 g/10 min. The supernatant is removed and the pellet is resuspended in 1 mL of solution E. PEG precipitation is repeated and the pellet is dissolved in 1 mL of solution G.
4. Controls
Infectivity control: Spike 1000 mL of pancrelipase sample with 125 FFU's of virus and precipitate virus. This control is designed to show that infectivity is not affected by virus precipitation.
Recovery control: Determined by PCR analysis of the DNA content prior to and after precipitation.
5. Infection of Cells
When using a 96-well semi-confluent cell, a volume of 270 μL (medium plus sample) was placed in each well. For each replicate, 4 different amounts were used (200, 100, 50 and 25 μL of sample, each topped off to a final volume of 270 μL). Three replicates per sample were made. The samples were incubated for 24-26 hr. at 37° C. (5% $CO_2$).
6. FFU Measurements
Supernatants were removed and stored separately at 4° C. The cells were fixed with solution H at room temperature for 15 minutes. Solution H was removed and the cells were washed with solution A. Solution A was removed and solution I was added. The cells were incubated for 15 minutes at RT and solution I was removed. The cells were washed twice with solution A. The 3C9 monoclonal antibody solution was diluted in solution J to a final concentration of 2%; 50 μL per well was added to the cells. The cells were incubated for 1 hour at RT and washed with solution A twice; then 50 μL of 1/1000 dilution of anti-mouse Alexafluor 488 conjugated antibody was added to the cells (Molecular Probes Invitrogen, Carlsbad, Calif.). The cell plates were incubated for one hour at RT in the dark and washed twice with solution A. FFU's ("green fluorescence") were counted using a fluorescent microscope (Broadspectra UV lamp, excitation at 488, specify filters). Five (5) replicates per sample were made.
7. Calculations
Counts were reported in table form. Results were expressed in FFU's/g of sample using counts at a dilution.

Example 6

Detection of PPV Nucleic Acid and Quantitative Analysis

A. Compounds Tested
Pancrelipase powder and minitablets were tested for the presence of PPV nucleic acid and quantitative analysis using PCR. Total PPV nucleic acid load was determined using quantitative PCR. A standard curve is established using known quantities of shortened amplicons and is used to quantify the number of DNA copies contained in a sample.
B. Materials, Techniques, and Equipment
1. Equipment
While any suitable thermocycler can be used for nucleic acid amplifications and quantitative PCR, a Hybaid Touch Down PCR machine was used in the reactions described herein.

2. Reagents and Solutions

The following solutions were used in the nucleic acid amplification and PCR reactions described herein.

Solution A: TRIS-HCl 100 mM, pH 8

Solution B: lysis buffer: 6M guanidium isothyocyanate, 10% triton X100, 100 mM sodium acetate (pH 5.2-5.5).

Solution C: polyA, 10 mg/mL.

Roche Diagnostic kit catalogue No.: 1 858 874 and for lysis solution kit: 1 754785.

Mimic A amplicon: Shortened version of viral target amplicon was created by deletion of nucleotide bases between 863 and 903 in the PPV sequence. After PCR amplification by using Primer A and B this fragment was cloned into the EcoRV site of the pBluescriptII KS+ plasmid (Stratagene). This recombinant plasmid has been amplified in *E. coli* SURE2 strain.

C. Protocols

1. DNA Extraction

Four grams of enzyme sample were dissolved in less than 40 mL of solution A and agitated overnight. The volume was adjusted to 40 mL (forming sample suspension). 20 µL of solution C was added to 25 mL of solution B. 300 µL of this solution was added to 200 µL of sample suspension and mixed. This mixture was incubated for 10 min at 70° C. 125 µL of isopropanol was added to the incubated mixture, the mixture was vortexed and transferred to a High-Pure Roche filter tube (Roche High Pure PCR Product Purification Kit, Roche Molecular Diagnostics, Pleasanton, Calif.). The mixture was centrifuged for 1 min. at 8000 g at RT. The filter was rinsed with 500 µL of wash buffer I and centrifuged for 1 min. at 8000 g. The filter was rinsed with 450 µL of wash buffer II and centrifuged for 1 min. at 8000 g. The rinse with wash buffer II was repeated and the mixture was centrifuged for 1 min. at 13,000 g. The High-Pure filter tube was transferred to a 1.5 mL centrifuge tube and 50 µL of water was added to the filter tube for elution of the DNA. The tubes were centrifuged for 1 min. at 8000 g to transfer the eluted DNA solution to the 1.5 mL tube. The filter tube was discarded. This extraction method is derived from Roche High Pure PCR Product Purification Kit. (Roche Diagnostic kit Cat. No 1 858 874 and kit 1 754785 for lysis solution, Roche Molecular Diagnostics, Pleasanton, Calif.).

D. Controls

For Standard PCR:

Positive extraction control: preparation of lab strain of PPV (NADL-2)

Negative extraction control: water for infection.

For Quantitative PCR:

Sample without Mimic A.

E. PCR Conditions

Program

| Denaturation | 95° C./5 min |
| --- | --- |
| Amplification (35 cycles) | 95° C./30 sec |
| | 72° C./30 sec |
| | 72° C./50 sec |
| Extension | 72° C./9 min |
| Stand-by | RT |

Amplification Conditions

| | Stock conc. | Final conc. | Volume (µL) |
| --- | --- | --- | --- |
| Water for injection | | | 35.85 |
| DNTP | 10 mM | 200 µM | 1 |
| Reaction Buffer + MgCl$_2$ | 10 X | 1 X | 5 |
| MgCl$_2$ | 20 mM | 3.5 mM | 3.75 |
| Sample (extracted DNA) | 50 µM | 1 µM | 2 |
| Primer A | 50 µM | 1 µM | 1 |
| Primer B | 50 µM | 2.0 units | 1 |
| Enzyme | 5 units/µL | | 0.4 |
| Final Volume | | | 50 |

Primers

```
Primer A
AGTGGGTATCGCTACTAACCTACACTC      (SEQ ID NO: 3)

Primer B
GATCTGTCATCATCCAGTCTTCTATGC      (SEQ ID NO: 4)
```

F. Visualization of PCR Products

PCR products were visualized after electrophoresis of 10 µL samples on a 1.8% agarose gel in TAE buffer 1× using ethidium bromide (EtBr) stain.

G. Standard PCR

Standard PCR was performed on extracted samples to confirm the presence of PPV DNA and on positive and negative extraction controls to confirm the absence of contamination and efficiency of extraction.

The goal in the set-up of the MIMIC is to have a known amount of competitor DNA fragment which is co-amplified with the PPV target sequence with the same efficiency by using the same primers and can be distinguished from the target molecule, e.g. by its size. The intervening sequences in the amplicons were established to have identical amplification efficiencies. Experimentally, PCR reaction tubes containing the target samples are spiked with a dilution series of the competitor fragment. When the molar ratio of PCR products generated from target and competitor is equal to one, the amount of target is equal to the competitor. Since the amount of competitor is known, the amount of target can thus be determined.

The MIMIC sequence is:

```
                                              (SEQ ID NO: 5)
AGTGGGTATC GCTACTAACC TACACTCGGA AATATGATTG

CTTACTACTT CCTAAATAAA AAAAGAAAGA CAACTGAAAG

AGAGCATGGA TATTATCTCA GCTCAGATTC TGGCTTCATG

ACAAATTTCT TAAAAGAAGG CGAGAGACAC TTAGTCAGTC

ACCTATTTAC TGAAGCAAAT AAACCTGAAA CTGTGGAAAC

AACGGTTACT ACAGCTCAGG AAGCCAAAAG AGGCAGAATA

CAAACAAAAA AAGAAGTAAG CATAAAATGC ACAATAAGAG

ACTTGGTTAA TAAAAGATGT ACTAGCATAG AAGACTGGAT

GATGACAGAT C
```

It was observed that this MIMIC sequence is optimal for Hybaid PCR equipment. For other equipment, we have observed other optimal sequences.

In italics are the sequences that hybridize the MIMIC primers. This sequence is cloned in a pBluescript vector so that large quantities can be prepared which in turn can be easily and precisely quantified.

The total length of this MIMIC amplicon is 331 base-pairs and is easily distinguished from the PPV amplicon with 372 base-pairs by agarose gel electrophoresis. The relative amounts are established by densitometry taking into account the relative molar masses of the amplicons.

H. Quantitative PCR

Quantitative PCT was performed in two steps. The first quantitative PCR provides an estimate of genome copies. The second quantitative PCR is intended to obtain a more precise value. Using primers A and B on the reference viral genome, an amplicon of 372 nucleotides was obtained. Amplicon Mimic A was generated using the same primers but due to an internal deletion, the Mimic A is 41 nucleotides shorter. This Mimic A serves as a competitor in the PCR reaction and is an internal standard used to quantitate genome copies of samples. The first PCR is made using 10-fold dilutions of the Mimic A internal standard while keeping the sample concentration constant. The second PCR is made using a more precise 2-fold dilution to obtain quantitative results. The control made of sample without mimic is run in parallel with the samples containing Mimic A to confirm there was no contamination with Mimic A.

The ratio of competing bands is determined by densitometry using any suitable equipment.

I. Calculations and Reporting of Results

Relative density of a DNA band corresponding to the sample is transformed into concentration using the calibration curve made using the different dilutions of internal standard. Results are reported in genome equivalents/gram of sample, as shown below.

Total PPV Recovery

TABLE 7

| Sample # | % of total genomic copy recovery in infectivity test |
| --- | --- |
| 1 | 63.8 |
| 2 | 85.1 |
| 3 | 75.3 |
| 4 | 98.4 |
| 5 | N/A |
| 5 | N/A |
| Mean | 80.5 |
| SD | 14.7 |

Note 1)
81% average recovery of total genome copies is good since results are expressed in log.
Note 2)
A SD of only 15% on average recovery shows good reproducibility.
Note 3)
Total PPV in replicates 2 and 4 show excellent reproducibility.

Infectious PPV Recovery in Spiked Pancrelipase Samples

TABLE 8

| Samples | Recovery of infectious PPV from spiked samples - corrected for matrix baseline (%)[1] | | | |
|---|---|---|---|---|
| | 200 μL/well | 100 μL/well | 50 μL/well | 25 μL/well |
| 1 | 26 | 45 | 18 | 35 |
| 2 | 44 | 72 | 108 | 108 |
| 3 | 26 | 36 | 54 | 24 |

TABLE 8-continued

| Samples | Recovery of infectious PPV from spiked samples - corrected for matrix baseline (%)[1] | | | |
|---|---|---|---|---|
| | 200 μL/well | 100 μL/well | 50 μL/well | 25 μL/well |
| 4 | 41 | 63 | 60 | 84 |
| 5 | 44 | 84 | 96 | 144 |
| Mean/recovery | 35.7 | 50.0 | 67.2 | 79.2 |
| SD | 9.4 | 19.5 | 35.8 | 49.9 |

[1]Average ffu from spiked sample corrected for baseline/theoretical number of ffu/well spiked
Note 1)
The average recovery is between 36-79%, but variability is relatively low for the best dilutions.

Example 7

A. Infectivity Assays Using the PPV Infectivity Method

One gram of pancrelipase sample was dissolved to 10 mL of 100 mM Tris-HCl, pH 8.0. A positive infectivity control sample was prepared by adding $10^5$ $FFID_{50}$ PPV (strain NADL-2) to 1 g of pancrelipase to 10 mL 100 mM Tris-HCl, pH 8.0. The samples were mixed for different times (0, 0.5, 1, 2, 24, 48, 72 and 168 hours) at room temperature. Samples prepared in duplicate. The dissolved samples were clarified with 3 consecutive chloroform extraction steps (3×4 mL chloroform). Following the chloroform extraction, the remaining upper phase was precipitated with the PEG stock solution. After resuspension of the pellets in Tris buffer, the PEG precipitation was repeated. The second PEG pellets were resuspended in 10 mL tissue culture medium (DMEM, 6% FBS, 50 ug/mL streptomycin). The dissolved samples were clarified with a chloroform extraction steps (5 mL chloroform). Following the chloroform extraction, the remaining upper phase was transferred to sterile tubes and store at 4° C. The stock solutions, buffers, and method details are the same as those described in Example 5, unless otherwise noted.

PPV infectivity was determined by using serial half-log (1:3.2) dilution series of the extracted PEP sample, then transferred to 8 replicate wells of a 96-well plate semi-confluent ST cells (ATCC: CRL-1746). Infectious viruses were detected by immunofluorescence (Fluorescence Focus Infectious Dose, FFID) after a 6 day incubation period. Infectious Doses were calculated according to the Karber formula:

$$FFID_{50}=10^{(D-0.5d+d(S))}$$

D=$\log_{10}$ of the highest dilution demonstrating 100% infection, d=$\log_{10}$ of the dilution factor and S=the ratio of the total number of wells with infection to the number of wells per dilution.

All data were recalculated for 1-gram dry pancrelipase sample after the consideration of sample concentrations, volumes and dilutions.

B. Results and Discussion

The resuspension step of the PEP Extraction was assayed to demonstrate the stability of the PPV virus in PEP suspension. For the PEP endogenous PPV (unspiked) as well as for the $10^5$ PPV spiked PEP, we have demonstrated no significant difference for the PPV virus stability in freshly resuspended to 2 hour of resuspension. At 24 hours and more of resuspension, losses of more than 1 log have been obtained for the unspiked and spiked PEP samples.

Optimally, the PEP resuspension step of the present invention has to should be less than or equal to 4 or 2 hours in order to minimize the loss of PPV virus titer.

TABLE 9

Summary of results for PPV content and infectivity of PEP samples using the PPV infectivity method.

| PEP ± PPV Virus | Incubation time (hr) | Virus titer ($Log_{10}FFID_{50}$) |
|---|---|---|
| Unspiked | 0 | 2.9 |
| | 0.5 | 2.4 |
| | 1 | 2.5 |
| | 2 | 3.3 |
| | 24 | 2.2 |
| | 48 | ≤2.0 |
| | 72 | ≤2.0 |
| | 168 | ≤2.0 |
| 5 $Log_{10}FFID_{50}$ NADL-2/g PEP | 0 | 4.7 |
| | 0.5 | 4.4 |
| | 1 | 4.4 |
| | 2 | 4.9 |
| | 24 | 3.8 |
| | 48 | 3.7 |
| | 72 | 3.4 |
| | 168 | 3.3 |

Example 8

A. Infectivity Assays Using the $FFID_{50}$ Method

One gram of each pancrelipase sample was dissolved in 10 mL Tris buffer. The dissolved sample was clarified with 3 consecutive chloroform extraction steps (3×–3 mL chloroform). Following the chloroform extraction, six ml of the remaining upper phase was precipitated with the PEG stock solution, in one ml aliquots. After resuspension of the pellets in Tris buffer, the PEG precipitation was repeated. The second PEG pellets were resuspended in only 1.5 mL tissue culture medium instead of the 6 mL original volume, concentrating the sample four times. Viral DNA was purified from 0.2 mL aliquots of the concentrated samples. The stock solutions, buffers, and method details are the same as those described in Example 5, unless otherwise noted.

PPV infectivity was determined by using 4 times dilution series of 0.1 mL purified samples (in 6 parallels). Infectious viruses were detected by immunofluorescence (Fluorescence Focus Infectious Dose, FFID) after a 5 day incubation period. Infectious Doses were calculated according to the Karber formula:

$$FFID_{50}=10^{(D-0.5d+d(S))}$$

$D=log_{10}$ of the highest dilution demonstrating 100% infection, $d=log_{10}$ of the dilution factor and $S=$the ratio of the total number of wells with infection to the number of wells per dilution.

All data were recalculated for 1-gram dry pancrelipase sample after the consideration of sample concentrations, volumes and dilutions.

Infectivity data measured using $FFID_{50}$ were also determined in separate experiments for a 10 day incubation period. Infectivity data measured using $TCID_{50}$ data were established by monitoring the cytopathic effects (CPE) at 5 and 10 days post infection.

B. Results and Discussion

Concentration of the samples using low speed centrifugation during the purification eliminated the majority of remaining impurities from the final preparations. This step allows both an easier quantification of viral DNA from the concentrated samples and also reduces the remaining toxicity. Additionally, the quality of samples isolated from the two-step PEG purification makes an ammonium sulfate precipitation step prior to the PEG precipitations (the three-step method) unnecessary, or optional. It is noted that use of an ammonium sulfate step can produce contamination at micromolar levels that could affect the infectivity assay by inhibiting endocytosis, which is important for the parvovirus infection. Thus, when the three-step ammonium sulfate method is utilized, a further purification step may be required. Utilizing purified samples from the two-step method as described provided quantitative PCR results on concentrated samples that were previously unmeasurable: See for example sample 5.

The two-step PEG precipitation method of the present invention provides a significantly improved detection method for both the sensitivity and the reproducibility of determining the PPV infectivity. Additionally, the robustness and consistency of the new assay is especially useful, because the samples with the highest level of infectious virus were always positive at the lower dilutions.

Incubation for longer than 5 days of the prepared samples with test cells did not increase the sensitivity of the $FFID_{50}$ assay. There was only one case when virus could be detected after 10 days of incubation with the sample but not after 5 days. The longer incubation period was somewhat more beneficial for the $TCID_{50}$ assays. However, the immunofluorescence based method ($FFID_{50}$) was more sensitive and reliable than the CPE based $TCID_{50}$ assay (as shown in Table 10). Generally, $FFID_{50}$ numbers were at least 2-5 times higher than the results of $TCID_{50}$ assay. Additionally, there was a greater reproducibility for the IF method because the infected wells were more evenly distributed than in the case of the CPE readings. Furthermore, the chance of contamination is reduced when the incubation period is shorter during a cell culture protocol.

To summarize the infectivity results in Table 11, infectious virus was detected in 14 out of 20 investigated samples (70%). One of the 14 samples had some cytostatic effect that could be noticed in the undiluted purified samples (Table 11). This effect could have reduced the absolute number for the infectivity. Four samples did not show any sign of toxicity and they were negative after 5 days using the $FFID_{50}$ and the $TCID_{50}$ assays (5 and 10 days). However, one of them may contain a very low amount of infectious virus, as shown after an incubation of 10 days using $FFID_{50}$. The two remaining samples contained a low amount of cytotoxicity after the two-step purification, as shown by cell killing at low dilutions.

An approximation method was used for the calculation of the low infectivity samples. The Karber formula requires the establishment of a dilution that displays 100% infection. However, some samples did not have full infection even at the undiluted concentration. It was assumed that four times concentration would give 100% infection if the undiluted sample demonstrated infectivity in any well. For example, the following equation can be applied for a sample that contains only one positive well at the undiluted concentration:

$$log_{10}(1/4)-0.5 \times log_{10}(4)+log_{10} \times (6/6+1/6)=-0.602-(0.602/2)+0.602\times(7/6)=-0.2006$$

$$FFID_{50}=10.^{-0.2006}=0.6299.$$

From this formula, it is predicted that a 0.1 mL titration sample and 100 mg/mL sample concentration, one-gram sample would contain 62.99 infectious particles. This is estimated to be the lowest concentration of virus that can be measured by this particular assay, if the sample does not contain appreciable levels of inhibitory materials. Typically, the assay is repeated several times in parallel (typically each dilution is performed in six parallel wells) to adequately quantify the level of infectious viruses. However, for those samples that contains more than 1000 infectious viruses in a one-gram dry material sample and exhibits no major discrepancy among the parallels of a single assay, provide acceptable results with one test assay. Among the investigated samples, 9 contained more than 1000 infectious particles in a one-gram sample.

It is also noted herein that any type of enzyme sample can be tested using the methods of the present invention, including samples that are in powder form, tablet form, capsule form, those that have been heated or not those that are coated or not coated, and samples of any concentration or mixtures.

TABLE 10

Summary of Results for PPV Content and Infectivity of Tested Samples

| Sample # | Form | GE/g | Infectivity ($FFID_{50}/g$) |
|---|---|---|---|
| 1 | pellets | $2.89 \times 10^8$ | 0* |
| 2 | capsules | $1.71 \times 10^8$ | 0* |
| 3 | capsules | $1.60 \times 10^8$ | 0* |
| 4 | powder | $2.07 \times 10^7$ | $5.04 \times 10^2$ |
| 5 | uncoated tablets | $6.76 \times 10^6$ | $2.00 \times 10^2$ |
| 6 | coated microtablets | $2.33 \times 10^8$ | $8.00 \times 10^2$ |
| 10 | mix before tableting | $4.89 \times 10^8$ | $2.02 \times 10^3$ |
| 11 | microtablets | $1.35 \times 10^7$ | $4.00 \times 10^{2**}$ |
| 12 | uncoated pellets | $1.84 \times 10^8$ | $1.00 \times 10^2$ |
| 13 | coated pellets | $4.09 \times 10^8$ | 0*** |
| 14 | uncoated minipellets | $7.74 \times 10^8$ | $4.06 \times 10^4$ |
| 15 | uncoated minipellets | $1.48 \times 10^8$ | $2.02 \times 10^3$ |
| 15n | powder | $1.64 \times 10^8$ | $1.61 \times 10^4$ |
| 20 | capsules | $1.52 \times 10^8$ | 0*** |
| 21-23 | pellets | $1.57 \times 10^8$ | $1.02 \times 10^4$ |
| 22 | capsules | $3.69 \times 10^8$ | 0* |
| 24 | pellets | $3.05 \times 10^7$ | $4.03 \times 10^3$ |
| 38 | high enzyme concentratum; powder | $2.09 \times 10^8$ | $2.56 \times 10^4$ |
| 39 | high enzyme concentratum; powder | $2.06 \times 10^8$ | $3.23 \times 10^4$ |
| 44 | high enzyme concentratum; powder | $2.08 \times 10^8$ | $1.61 \times 10^4$ |

0: negative test results;
*no sign of cytotoxicity;
**partial cytostatic effect;
***cytotoxicity was observed at low dilution of the sample.

TABLE 11

Measurement of PPV Infectivity by $FFID_{50}$ and $TCID_{50}$ Assays

| Sample # | GE/g | $FFID_{50}/g$ | | $TCID_{50}/g$ | |
|---|---|---|---|---|---|
| | | 5 days | 10 days | 5 days | 10 days |
| 1 | $2.89 \times 10^8$ | 0* | 0* | 0* | 0* |
| 2 | $1.71 \times 10^8$ | 0* | $1.00 \times 10^2$ | 0* | 0* |
| 3 | $1.60 \times 10^8$ | 0* | 0* | 0* | 0* |
| 4 | $2.07 \times 10^7$ | $5.04 \times 10^2$ | $4.00 \times 10^2$ | $1.26 \times 10^2$ | $2.00 \times 10^2$ |
| 5 | $6.76 \times 10^6$ | $2.00 \times 10^2$ | $2.52 \times 10^2$ | $6.30 \times 10^1$ | $7.94 \times 10^1$ |
| 6 | $2.33 \times 10^8$ | $8.00 \times 10^2$ | $3.20 \times 10^3$ | $3.18 \times 10^2$ | $2.54 \times 10^3$ |
| 10 | $4.89 \times 10^8$ | $2.02 \times 10^3$ | $5.08 \times 10^3$ | $3.18 \times 10^2$ | $4.00 \times 10^2$ |
| 11 | $1.35 \times 10^7$ | $4.00 \times 10^{2**}$ | $1.27 \times 10^{3**}$ | 0** | $1.00 \times 10^{2**}$ |
| 12 | $1.84 \times 10^8$ | $1.00 \times 10^2$ | $2.00 \times 10^2$ | 0* | $7.94 \times 10^1$ |
| 13 | $4.09 \times 10^8$ | 0*** | 0*** | 0*** | 0*** |
| 14 | $7.74 \times 10^8$ | $4.06 \times 10^4$ | $2.03 \times 10^4$ | $1.61 \times 10^4$ | $1.61 \times 10^4$ |
| 15 | $1.48 \times 10^8$ | $2.02 \times 10^3$ | $1.27 \times 10^3$ | $5.04 \times 10^2$ | $6.35 \times 10^2$ |
| 15n | $1.64 \times 10^8$ | $1.61 \times 10^4$ | $2.56 \times 10^4$ | $5.08 \times 10^3$ | $8.06 \times 10^3$ |
| 20 | $1.52 \times 10^8$ | 0*** | 0*** | 0*** | 0*** |
| 21-23 | $1.57 \times 10^8$ | $1.02 \times 10^4$ | $5.08 \times 10^3$ | $3.20 \times 10^3$ | $2.54 \times 10^3$ |
| 22 | $3.69 \times 10^8$ | 0* | 0* | 0* | 0* |
| 24 | $3.05 \times 10^7$ | $4.03 \times 10^3$ | $2.54 \times 10^3$ | $3.20 \times 10^3$ | $1.27 \times 10^3$ |
| 38 | $2.09 \times 10^8$ | $2.56 \times 10^4$ | $2.03 \times 10^4$ | $6.40 \times 10^3$ | $4.03 \times 10^3$ |
| 39 | $2.06 \times 10^8$ | $3.23 \times 10^4$ | $2.03 \times 10^4$ | $6.40 \times 10^3$ | $1.28 \times 10^4$ |
| 44 | $2.08 \times 10^8$ | $1.61 \times 10^4$ | $2.03 \times 10^4$ | $6.40 \times 10^3$ | $8.06 \times 10^3$ |

0: negative test results;
*no sign of cytotoxicity;
**partial cytostatic effect;
***cytotoxicity was observed at low dilution of the sample.

SUMMARY

Quantification of PPV DNA by MIMIC PCR showed that there are moderate to significant amounts of virus particles in the tested pancrelipase products. The results provided herein show that the present methods provide efficient and reproducible PPV assay methods for the quantification of infectious virus in the tested enzyme samples, which are representative of commercially available exocrine enzyme products. Infectivity cannot be determined using direct analysis of any of the diluted samples.

The present invention thus provides methods for determining viral infectivity and content in a pancreatic enzyme preparation (PEP). In certain embodiments, the invention relates to detecting infectious porcine parvovirus (PPV) and determining PPV content in PEPs, including pancrelipase preparations. The two and three step chloroform PEG precipitation methods described herein provide reproducible and efficient methods for determining the porcine parvoviral (PPV) content and PPV infectivity of pancreatic enzyme preparations and supplements, including pancrelipase. These methods are particularly useful because they balance the ability to preserve the infectious non-enveloped virus with the ability to eliminate the toxic enzyme materials from the PEP samples and provide an extremely useful and cost-effective way to identify enzyme preparations (e.g., pancrelipase) that have a desirable, low threshold of infectious virus for further manufacture and potentially for batch production of pharmaceutical products. These methods are useful for analyzing enzyme preparations generally, as well as for analyzing preparations for incorporating into batches for production of pharmaceutical dosage formulations.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

What is claimed:

1. A method for producing a pharmaceutical product containing a pancreatic enzyme preparation having a porcine parvovirus (PPV) viral load below a threshold level comprising:
   a. obtaining a sample from a pancreatic enzyme preparation;
   b. detecting the load of porcine parvovirus in the sample comprising:
      i. extracting the sample at least two times with chloroform prior to precipitation producing a clarified sample with an upper phase and a lower phase;
      ii. precipitating an aliquot of the upper phase from step i) with polyethylene glycol (PEG);
      iii. suspending the product from step ii) in a buffer;
      iv. precipitating the product from step iii) with PEG;
      v. suspending the product from step iv) in an aqueous solution;
      vi. optionally extracting the product from step v) with chloroform producing a clarified sample with an upper phase and a lower phase; the upper phase forming a purified solution; and
      vii. determining the load of porcine parvovirus in the solution; and
   c. producing a pharmaceutical product with the remainder of the pancreatic enzyme preparation if the porcine parvovirus viral load measured in step b) is below a fluorescence focus infectious dose ($FFID_{50}$) PPV viral load of about $10^5$ $FFID_{50}$.

2. The method of claim 1, wherein the PEG is PEG 8000.

3. The method of claim 1, wherein the pancreatic enzyme composition is pancrelipase or pancreatine comprising various ratios of at least three enzymes selected from the group consisting of lipase, amylase, and protease.

* * * * *